(12) United States Patent
Shih et al.

(10) Patent No.: US 10,604,513 B2
(45) Date of Patent: Mar. 31, 2020

(54) PYRIDONE DERIVATIVE COMPRISING HETEROATOMIC RING BUTANE SUBSTITUENT, FOR TREATING FIBROSIS AND INFLAMMATORY DISEASES

(71) Applicant: SHIJIAZHUANG SAGACITY NEW DRUG DEVELOPMENT CO., LTD., Hebei (CN)

(72) Inventors: Neng-yang Shih, Shanghai (CN); Bin Chen, Shanghai (CN); Lei Zhang, Shanghai (CN); Jian Li, Shanghai (CN); Shuhui Chen, Shanghai (CN)

(73) Assignee: Shijiazhuang Sagacity New Drug Development Co., Ltd., Shijiazhuang (CN)

(*) Notice: Subject to any disclaimer, the term of this patent is extended or adjusted under 35 U.S.C. 154(b) by 0 days.

(21) Appl. No.: 16/093,376

(22) PCT Filed: Apr. 14, 2017

(86) PCT No.: PCT/CN2017/080599
§ 371 (c)(1),
(2) Date: Oct. 12, 2018

(87) PCT Pub. No.: WO2017/177974
PCT Pub. Date: Oct. 19, 2017

(65) Prior Publication Data
US 2019/0062315 A1 Feb. 28, 2019

(30) Foreign Application Priority Data

Apr. 14, 2016 (CN) .......................... 2016 1 0232306

(51) Int. Cl.
| | | |
|---|---|---|
| *C07D 405/04* | (2006.01) | |
| *C07D 409/14* | (2006.01) | |
| *A61K 31/4436* | (2006.01) | |
| *A61K 31/4427* | (2006.01) | |
| *A61P 1/16* | (2006.01) | |
| *A61P 11/00* | (2006.01) | |
| *C07D 417/14* | (2006.01) | |

(52) U.S. Cl.
CPC ........ *C07D 405/04* (2013.01); *A61K 31/4427* (2013.01); *A61K 31/4436* (2013.01); *A61P 1/16* (2018.01); *A61P 11/00* (2018.01); *C07D 409/14* (2013.01); *C07D 417/14* (2013.01)

(58) Field of Classification Search
CPC .......................... C07D 405/12; C07D 405/04
See application file for complete search history.

(56) References Cited

U.S. PATENT DOCUMENTS

| | | | |
|---|---|---|---|
| 8,969,347 B2 | 3/2015 | Kossen et al. | |
| 9,359,379 B2 | 6/2016 | Buckman et al. | |
| 2014/0094456 A1* | 4/2014 | Buckman ............. | C07D 213/64 514/227.8 |
| 2014/0107110 A1* | 4/2014 | Buckman ............. | C07D 513/04 514/227.8 |

FOREIGN PATENT DOCUMENTS

| | | |
|---|---|---|
| CN | 102099036 A | 6/2011 |
| CN | 102786467 A | 11/2012 |
| CN | 104822687 A | 8/2015 |
| WO | 2009149188 A1 | 12/2009 |
| WO | 2014055548 A1 | 4/2014 |
| WO | 2015153683 A1 | 10/2015 |

OTHER PUBLICATIONS

May 12, 2017 International Search Report issued in International Patent Application No. PCT/CN2017/080599.
May 12, 2017 Written Opinion of the International Searching Authority issued in International Patent Application No. PCT/CN2017/080599.
Berge et al., Pharmaceutical Salts, Journal of pharmaceutical Science 66: 1-19 (1977).
Maehr, J.Chem.Ed.1985, 62: 114-120. 1985,62: 114-120.
Remington:The Science and Practice of Pharmacy, 21st Ed., Lippincott, Williams &Wilkins (2005).
Extended European Search Report issued in the counterpart European application No. 17781950.5 dated Aug. 8, 2019.
Na Sun et al., "Pharmacokinetic and pharmacometabolomic study of pirfenidone in normal mouse tissues using high mass resolution MALDI-FTICR-mass spectrometry imaging", Histochemistry and Cell Biology, 2016, vol. 145, Issue 2, pp. 201-211.

* cited by examiner

*Primary Examiner* — Rei Tsang Shiao
(74) *Attorney, Agent, or Firm* — Harness, Dickey & Pierce, P.L.C.

(57) ABSTRACT

Disclosed is a compound for treating fibrosis-related diseases, and specifically disclosed are the compound represented by formula (I) and a pharmaceutically acceptable salt thereof.

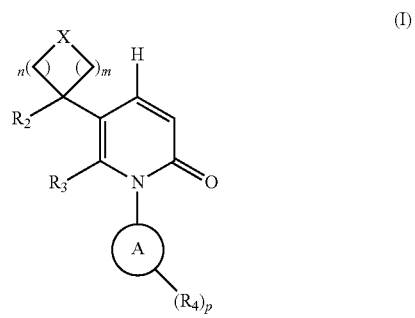

21 Claims, 3 Drawing Sheets

PYRIDONE DERIVATIVE COMPRISING HETEROATOMIC RING BUTANE SUBSTITUENT, FOR TREATING FIBROSIS AND INFLAMMATORY DISEASES

CROSS-REFERENCE TO RELATED APPLICATIONS

This application is a 371 U.S. National Stage of International Application No. PCT/CN2017/080599, filed Apr. 14, 2017, which claims priority to Chinese Patent Application No. 201610232306.9, filed Apr. 14, 2016. The entire disclosures of the above applications are incorporated herein by reference.

FIELD OF INVENTION

The present invention relates to a series of novel compounds for treating fibrosis-related diseases, and specifically relates to a series of compounds represented by formula (I) and pharmaceutically acceptable salts thereof.

BACKGROUND OF INVENTION

Tissue fibrosis is the major cause for disability and death related to a variety of diseases worldwide. According to relevant statistics, 45% of patients who died from various diseases in the United States can be attributed to tissue fibrosis hyperplasia-related diseases. The body organs are composed of two parts: parenchyma refers to the main structure and functional cells of organs (for example, hepatic parenchyma cell is hepatocyte), and mesenchyme consists of stromal cell and extracellular matrix (mainly have collagen, proteoglycan, saccharide, glycoprotein and elastin) which distributes between parenchymal cells and is mainly for mechanical support and connection. In addition, the extracellular matrix can constitute a microenvironment that maintains the physiological activities of cells, is a bridge for signal transduction, participates in a variety of physiological and pathological processes, and plays an important role in tissue repair and fibrosis. Damage caused by any cause can cause degeneration and death of tissue cells, and inflammation. If the damage is less, the normal parenchymal cells surrounding the damaged cells will proliferate and repair the damaged tissue, and this repair can be completely restored to normal structure and function. However, if the damage is larger or repeated damage, and exceeds the regenerative capacity of the surrounding parenchymal cells, the interstitial fibrous connective tissue (extracellular matrix) will proliferate massively to repair the defect tissue, that is, pathological changes of fibrosis occur. Therefore, fibrosis is essentially a repair response to tissue damage to protect the relative integrity of tissues and organs. Although the proliferating fibrous connective tissue repairs the defect, it does not have the structure and function of the original organ parenchymal cells. If this repair is overreacted, too strong and out of control, it will lead to fibrosis of organs and cause a decline of organ functions. Thus, fibrosis refers to the pathological process in which the parenchymal cells are necrotic due to inflammation, and the extracellular matrix in the tissue is abnormally increased and excessively deposited. The light one becomes fibrosis, and the severe one causes the destruction of the tissue structure and then the organ hardens. Among various fibrosis-related diseases, pulmonary fibrosis and liver fibrosis are the most common.

Idiopathic Pulmonary Fibrosis (IPF) is a typical chronic, progressive and fatal fibrotic interstitial pneumonia characterized by progressive dyspnea and a gradual decline in lung function, which quickly leads to respiratory failure and death. At least 5 million people worldwide suffered from this in 2008, 130,000 to 500,000 people only in the United States in 2010. About 48,000 new cases were reported and about 40,000 people died of IPF each year. The incidence of IPF is estimated to be 4.6-7.4/100,000, and 30,000 to 35,000 new cases are diagnosed each year. The incidence of smokers is much greater than that of non-smokers. The incidence of IPF can reach nearly 2.3% in people with a smoke history of 20-40 years. The incidence of males is higher than that of females. The 5-year individual survival rate of IPF is about 20%, and the mortality rate is much higher than that of many cancers, which is known as a cancer that is not cancer actually. Potential risk factors include occupational exposure and environmental pollution such as metals, animals, wood chips, smoking and smog.

The pathogenesis of IPF is complex and is generally thought to involve interactions between pro-inflammatory and pro-fibrotic pathways, but the exact mechanism is still unknown. In 2014, Roche's Pirfenidone and Boehringer Ingelheim's nintedanib were first approved in the United States, and annual sales peak of Pirfenidone is estimated to reach \$2 billion in 2019. The prognosis of IPF is poor at present, and treatment solutions are scarce. The marketing of these two new drugs gives confidence in the progression of IPF disease, and these two drugs are likely to be used to treat other fibrotic diseases. However, the development of novel IPF drugs gets continuously valued since there are still unsatisfied clinical demands for large quantity of patients.

CONTENT OF THE PRESENT INVENTION

The present invention provides a compound shown in formula (I)、a pharmaceutically acceptable salt and a tautomer thereof,

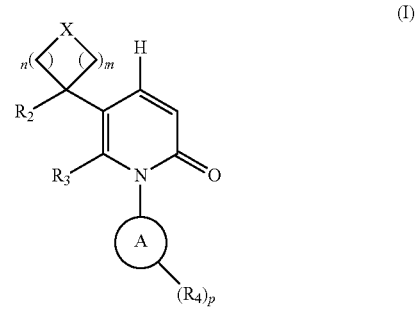

wherein,

X is selected from O、S、and N(R);

$R_2$ is selected from F、Cl、Br、I、OH、$NH_2$、CN、$NO_2$、COOH, or selected from the group consisting of $C_{1-6}$ alkyl and $C_{1-6}$ heteroalkyl, the $C_{1-6}$ alkyl and $C_{1-6}$ heteroalkyl are optionally substituted with 1, 2 or 3 of R;

$R_3$ is selected from H, or selected from the group consisting of $C_{1-6}$ alkyl and $C_{1-6}$ heteroalkyl, the $C_{1-6}$ alkyl and $C_{1-6}$ heteroalkyl are optionally substituted with 1, 2 or 3 of R;

$R_4$ is selected from F、Cl、Br、I、OH、$NH_2$、$NO_2$、CN、COOH, or selected from the group consisting of $C_{1-6}$ alkyl and $C_{1-6}$ heteroalkyl, the $C_{1-6}$ alkyl and $C_{1-6}$ heteroalkyl are optionally substituted with 1, 2 or 3 of R;

Ring A is selected from 5-10-membered aryl and 5-10-membered heteroaryl;

m is selected from 0、1 or 2;
n is selected from 0、1 or 2;
m and n are not selected from 0 simultaneously;
p is selected from 0、1、2 or 3;
R is selected from H、F、Cl、Br、I、OH、CN、NH$_2$、COOH、C(=O)NH$_2$, or selected from the group consisting of C$_{1-8}$ alkyl、C$_{1-8}$ heteroalkyl、C$_{3-6}$ cycloalkyl、3 to 6 membered heterocycloalkyl and C$_{3-6}$ cycloalkyl-C$_{1-3}$ alkyl, the C$_{1-8}$ alkyl、C$_{1-8}$ heteroalkyl、C$_{3-6}$ cycloalkyl、3 to 6 membered heterocycloalkyl and C$_{3-6}$ cycloalkyl-C$_{1-3}$ alkyl are optionally substituted with 1, 2 or 3 of R';
R' is selected from F、Cl、Br、I、OH、CN、NH$_2$、COOH、Me、Et、CF$_3$、CHF$_2$、CH$_2$F、NHCH$_3$、N(CH$_3$)$_2$;
hetero means hetero atom or hetero group, is selected from the group consisting of —C(=O)N(R)—、—N(R)—、—C(=NR)—、—S(=O)$_2$N(R)—、—S(=O)N(R)、—O—、—S—、=O、=S、—O—N=、—C(=O)—、—C(=O)—、—C(=S)—、—S(=O)—、—S(=O)$_2$— and —N(R)C(=O)N(R)—;
in any case above, the number of hetero atom or hetero group is independently selected from 1、2 or 3, respectively.

In certain embodiment of this invention, R is selected from H、F、Cl、Br、I、OH、CN、NH$_2$、COOH、C(=O)NH$_2$, or selected from the group consisting of C$_{1-3}$ alkyl, C$_{1-3}$ alkyl-O—、C$_{1-3}$ alkyl-S—、C$_{1-3}$ alkyl-NH—、N,N'-di(C$_{1-3}$ alkyl)amino、C$_{3-6}$ cycloalkyl and 3-6-membered heterocycloalkyl, the C$_{1-3}$ alkyl、C$_{1-3}$ alkyl-O—、C$_{1-3}$ alkyl-S—、C$_{1-3}$ alkyl-NH—z,109 N,N'-di(C$_{1-3}$ alkyl)amino、C$_{3-6}$ cycloalkyl and 3-6-membered heterocycloalkyl are optionally substituted with 1, 2 or 3 of R'.

In certain embodiment of this invention, R is selected from H、F、Cl、Br、I、OH、CN、NH$_2$、COOH、C(=O)NH$_2$、Me、Et、CF$_3$、CHF$_2$、CH$_2$F、NH(CH$_3$)、N(CH$_3$)$_2$.

In certain embodiment of this invention, the structural unit

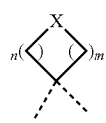

is selected from

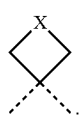

In certain embodiment of this invention, the structural unit

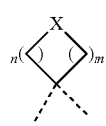

is selected from

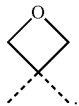

In certain embodiment of this invention, R$_2$ is selected from F、Cl、Br、I、OH、NH$_2$、CN、NO$_2$、COOH, or selected from the group consisting of C$_{1-3}$ alkyl optionally substituted with 1, 2 or 3 of R.

In certain embodiment of this invention, R$_2$ is selected from F、Cl、Br、I、OH、NH$_2$、CN、NO$_2$、COOH, or selected from Me optionally substituted with 1, 2 or 3 of R.

In certain embodiment of this invention, R$_2$ is selected from F、Cl、Br、I、OH、NH$_2$、CN、NO$_2$、COOH、Me.

In certain embodiment of this invention, R$_4$ is selected from F、Cl、Br、I、OH、NH$_2$、NO$_2$、CN、COOH, or selected from the group consisting of C$_{1-3}$ alkyl、C$_{1-3}$ alkoxy、C$_{1-3}$ alkylthio、NH(C$_{1-3}$ alkyl) and N,N'-di(C$_{1-2}$ alkyl)amino, the C$_{1-3}$ alkyl, C$_{1-3}$ alkoxy、C$_{1-3}$ alkylthio、NH(C$_{1-3}$ alkyl) and N,N'-di(C$_{1-2}$ alkyl)amino are optionally substituted with 1, 2 or 3 of R.

In certain embodiment of this invention, R$_4$ is selected from F、Cl、Br、I、OH、NH$_2$、NO$_2$、CN、COOH, or selected from the group consisting of Me and

the Me and

are optionally substituted with 1, 2 or 3 of R.

In certain embodiment of this invention, R$_4$ is selected from F、Cl、Br、I、OH、NH$_2$、NO$_2$、CN、COOH、Me、

In certain embodiment of this invention, ring A is selected from 5-6 membered aryl and 5-9 membered heteroaryl.

In certain embodiment of this invention, the ring A is selected from phenyl、pyridinyl、pyrazinyl、pyrimidyl、pyridaziny、pyrryl、imidazolyl、pyrazolyl、furyl、thienyl、oxazolyl、thiazolyl、isoxazolyl、isothiazolyl、triazolyl、benzothienyl.

In certain embodiment of this invention, the structural unit

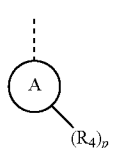

is selected from

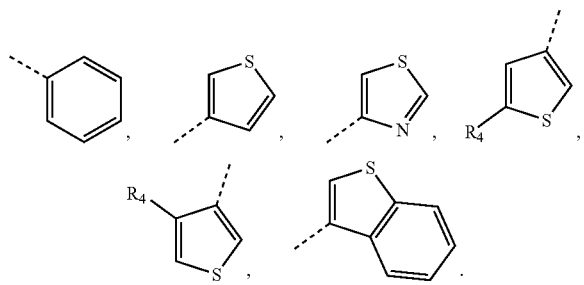

In certain embodiment of this invention, the structural unit

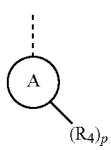

is selected from

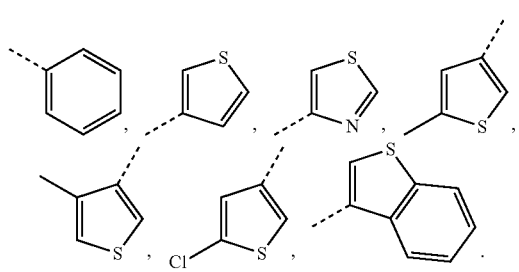

In certain embodiment of this invention, R is selected from H、F、Cl、Br、I、OH、CN、NH$_2$、COOH、C(=O)NH$_2$, or selected from the group consisting of C$_{1-3}$ alkyl、C$_{1-3}$ alkyl-O—、C$_{1-3}$ alkyl-S—、C$_{1-3}$ alkyl-NH—、N,N'-di(C$_{1-3}$ alkyl)amino、C$_{3-6}$ cycloalkyl and 3-6 membered heterocycloalkyl, the C$_{1-3}$ alkyl、C$_{1-3}$ alkyl-O—、C$_{1-3}$ alkyl-S—、C$_{1-3}$ alkyl-NH—、N,N'-di(C$_{1-3}$ alkyl)amino、C$_{3-6}$ cycloalkyl and 3-6 membered heterocycloalkyl are optionally substituted with 1, 2 or 3 of R', and other variables are as defined above.

In certain embodiment of this invention, R is selected from H、F、Cl、Br、I、OH、CN、NH$_2$、COOH、C(=O)NH$_2$、Me、Et、CF$_3$、CHF$_2$、CH$_2$F、NH(CH$_3$)、N(CH$_3$)$_2$, and other variables are as defined above.

In certain embodiment of this invention, the structural unit

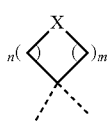

is selected from

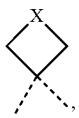

and other variables are as defined above.

In certain embodiment of this invention, the structural unit

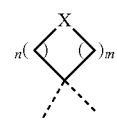

is selected from

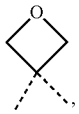

and other variables are as defined above.

In certain embodiment of this invention, R$_2$ is selected from F、Cl、Br、I、OH、NH$_2$、CN、NO$_2$、COOH, or selected from the group consisting of C$_{1-3}$ alkyl optionally substituted with 1, 2 or 3 of R, and other variables are as defined above.

In certain embodiment of this invention, R$_2$ is selected from F、Cl、Br、I、OH、NH$_2$、CN、NO$_2$、COOH, or selected from Me optionally substituted with 1, 2 or 3 of R, and other variables are as defined above.

In certain embodiment of this invention, R$_2$ is selected from F、Cl、Br、I、OH、NH$_2$、CN、NO$_2$、COOH、Me, and other variables are as defined above.

In certain embodiment of this invention, R$_4$ is selected from F、Cl、Br、I、OH、NH$_2$、NO$_2$、CN、COOH, or selected from the group consisting of C$_{1-3}$ alkyl、C$_{1-3}$ alkoxy、C$_{1-3}$ alkylthio、NH(C$_{1-3}$ alkyl) and N,N'-di(C$_{1-3}$ alkyl)amino, the C$_{1-3}$ alkyl、C$_{1-3}$ alkoxy、C$_{1-3}$ alkyl sulphanyl、NH(C$_{1-3}$ alkyl) and N,N'-di(C$_{1-3}$ alkyl)amino are optionally substituted with 1, 2 or 3 of R, and other variables are as defined above.

In certain embodiment of this invention, R$_4$ is selected from F、Cl、Br、I、OH、NH$_2$、NO$_2$、CN、COOH, or selected from the group consisting of Me and

the Me and

are optionally substituted with 1, 2 or 3 of R, and other variables are as defined above.

In certain embodiment of this invention, R$_4$ is selected from F、Cl、Br、I、OH、NH$_2$、NO$_2$、CN、COOH、Me、

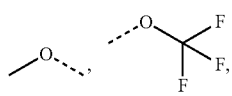

and other variables are as defined above.

In certain embodiment of this invention, the ring A is selected from 5-6 membered aryl and 5-9 membered heteroaryl, and other variables are as defined above.

In certain embodiment of this invention, the ring A is selected from phenyl、 pyridinyl、 pyrazinyl、 pyrimidyl、 pyridaziny、 pyrryl、 imidazolyl、 pyrazolyl、 furyl、 thienyl、 oxazolyl、 thiazolyl、 isoxazolyl、 isothiazolyl、 truazolyl、 benzothienyl、 and other variables are as defined above.

In certain embodiment of this invention, the structural unit

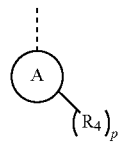

is selected from

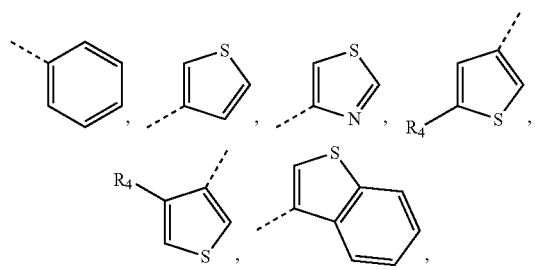

and other variables are as defined above.

In certain embodiment of this invention, the structural unit

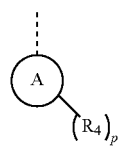

is selected from

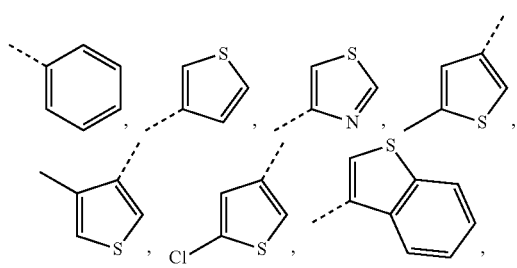

and other variables are as defined above.

In certain embodiment of this invention, the compound, the pharmaceutically acceptable salt and the tautomer thereof are selected from

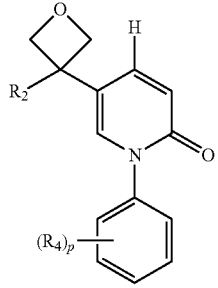
(I-1)

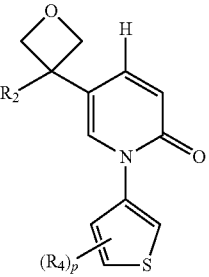
(I-2)

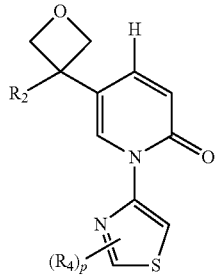
(I-3)

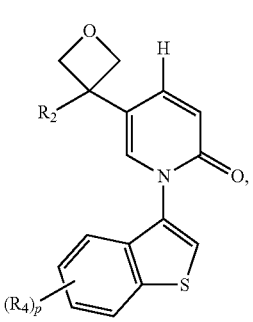
(I-4)

wherein, $R_2$、 $R_4$ and p are as defined above.

This present invention contains other embodiments which are combined arbitrarily by the aforesaid variables.

This present invention also provides compounds showed as formula below:

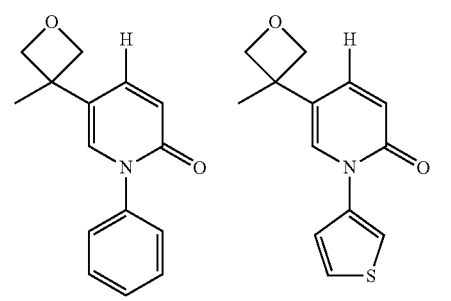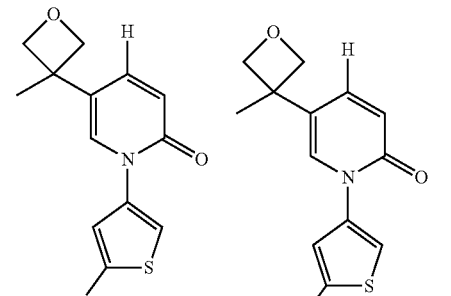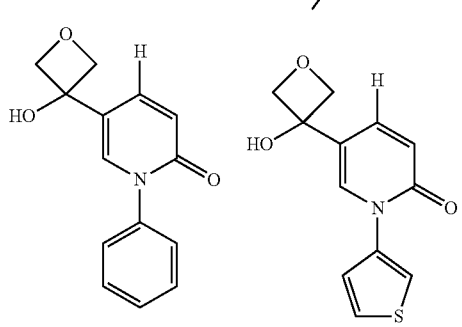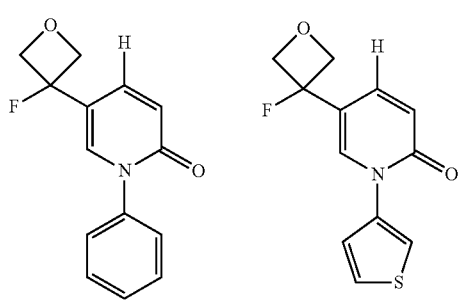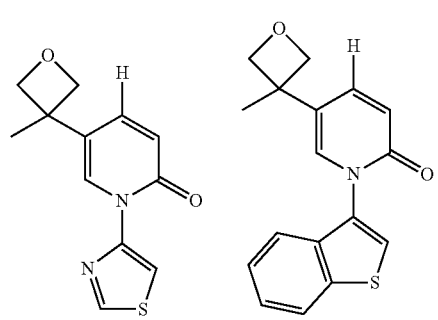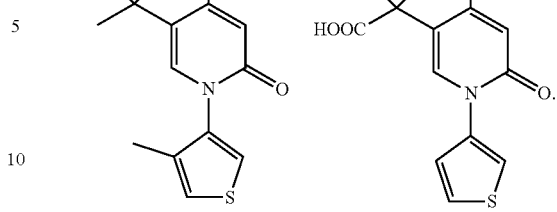

Another purpose of this present invention is to provide a kind of pharmaceutical composition comprising an effective amount of the compound or the pharmaceutically acceptable salt thereof and a pharmaceutically acceptable carrier.

Another purpose of the present invention is to provide a use of the compound or the pharmaceutically acceptable salt or the pharmaceutical composition in the preparation of a medicament for the treatment of fibrosis-related diseases.

In certain embodiment of this invention, the fibrosis-related diseases refer to idiopathic pulmonary fibrosis.

In certain embodiment of this invention, the fibrosis-related diseases refer to hepatic fibrosis Definitions and Explanations Unless otherwise stated, the terms and phrases used here have the meanings assigned thereto. One certain terms or phrases shouldn't be deemed as being uncertain or unclear without special definition, but should be understood according to normal meanings. Trade names used here refer to corresponding goods or their effective components.

$C_{1-12}$ is selected from $C_1$、$C_2$、$C_3$、$C_4$、$C_5$、$C_6$、$C_7$、$C_8$、$C_9$、$C_{10}$、$C_{11}$ and $C_{12}$; $C_{3-12}$ is selected from $C_3$、$C_4$、$C_5$、$C_6$、$C_7$、$C_8$、$C_9$、$C_{10}$、$C_{11}$ and $C_{12}$.

$C_{1-12}$ alkyl or hetero alkyl、$C_{3-12}$ cycloalkyl or hetero cycloalkyl、$C_{1-12}$ alkyl or hetero alkyl substituted with $C_{1-12}$ cycloalkyl or hetero cycloalkyl include, but not limited to $C_{1-12}$ alkyl、$C_{1-12}$ alkylamino、N,N-di($C_{1-12}$alky) amino、$C_{1-12}$ alkoxy、$C_{1-12}$ alkylacyl、$C_{1-12}$ carbalkoxy、$C_{1-12}$ alkylsulfonyl、$C_{1-12}$ alkylsulfinyl、$C_{3-12}$ cycloalkyl、$C_{3-12}$ cycloalkylamino、$C_{3-12}$ hetero cycloalkylamino、$C_{3-12}$ cycloalkoxy、$C_{3-12}$ cycloalkylacyl、$C_{3-12}$ cyclocarbalkoxy、$C_{3-12}$ cycloalkylsulfonyl、$C_{3-12}$ cycloalkylsulfinyl、5-12 members aryl or hetero aryl、5-12 members aralkyl or hetero aralkyl; methyl、ethyl、n-propyl、i-propyl、—CH$_2$C(CH$_3$)(CH$_3$)(OH)、cyclopropyl、cyclobutyl、propyl methylene、cyclopropyl acyl、benzyloxy、triflurine methyl、aminomethyl、hydroxy methyl、methoxyl、methylacyl、methoxycarbonyl、methyl sulfonyl、methyl sulfinyl、ethoxyl、ethylacyl、ethyl sulfonyl、ethoxycarbonyl、dimethylamino、diethylamino、dimethylaminocarbonyl、diethylaminocarbonyl; N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN, —CH$_2$CH(OH)(CH$_3$)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)CH$_3$ and phenyl, thiazolyl, biphenyl, naphthyl, cyclopentyl, furyl, 3-pyrrolinyl, pyrrolidyl, 1,3-dioxolanyl, pyrazolyl, 2-pyrrolinyl, pyrazolidinyl, imidazolyl, oxazolyl, thiazolyl, 1,2,3-azolyl, 1,2,3-triazolyl, 1,2,4-triazolyl, 1,3,4-thidiazolyl, 4H-pyranyl, pyridyl, piperidyl, 1,4-dioxanyl, morpholinyl, pyridazinyl, pyrimidyl, pyrazinyl, piperazinyl, 1,3,5-trithioohanyl, 1,3,5-triazinyl, benzofuryl, benzothienyl, indolyl, benzimidazolyl, benzothiazolyl, purinyl, quinolyl, isoquinolyl, cinnolinyl or quinoxalinyl;

The term "pharmaceutically acceptable" used herein is in allusion to those compounds, materials, compositions and/or dosages which are applied to contact to human and animal tissues without excessive toxicity, irritation, anaphylaxis, or other issues or complication, and suit to rational interest and risk ratio within the bounds of reliable medical judgment.

The term "pharmaceutically acceptable salt" refers to salt of the compounds in this invention which are prepared by compounds with certain substituents and relatively nontoxic acids or alkalis. When compounds contain relatively acidic functional group, alkalis-additive salts are prepared by enough alkalis contacting with these compounds in neutral form in pure solutions or appropriate inert solvents. Pharmaceutically acceptable alkalis-additive salts include sodium、 potassium、 calcium、 ammonium or magnesium salts, or analogous salts. When compounds contain relatively alkaline functional group, acid-additive salts are prepared by enough acids contacting with these compounds in neutral form in pure solutions or appropriate inert solvents. Examples of pharmaceutically acceptable acid-additive salts include inorganic acid salts, the aforesaid inorganic acids include hydrochloric acid、 hydrobromic acid、 nitric acid、 carbonic acid、 bicarbonate radical、 phosphoric acid、 monohydrogen phosphate、 dihydrogen phosphate、 sulphuric acid、 bisulfate、 hydroiodic acid、 phosphorous acid and so on; and organic acid、 the aforesaid organic acids include acetic acid、 propionic acid、 isobutyric acid、 maleic acid、 malonic acid、 benzoic acid、 succinic acid、 octandioic acid、 allomaleic acid、 lactate、 amygdalic acid、 alizaric acid、 benzenesulfonic acid、 p-methylbenzenesulfonic acid、 citric acid、 tartaric acid、 methylsulforic acid and so on; also include amino acid (like arginine) salts, and organic acid salts like glucuronic acid and so on (refer to Berge et al., "pharmaceutical Salts", Journal of pharmaceutical Science 66: 1-19 (1977)). The certain compounds containing alkaline and acidic functional groups in this invention can be transferred into any one of alkaline- or acidic-additive salts.

Preferably, salts contact with alkalis or acids in normal ways, and then maternal compounds are separated to give regenerated compounds in neutral form. The differences between maternal forms and various saline forms of compounds are certain physical properties, such as different solubility in polar solvents.

The term "pharmaceutically acceptable salts" used herein is derivatives of compounds in this invention, including, maternal compounds modified through salifying with acids or alkalis. Examples of pharmaceutically acceptable salts include, but are not limited to, alkali bases, such as inorganic acid salts or organic acid salts of amines, acid radicals, such as alkali metal salts or organic salts of carboxylic acids, and so on. Pharmaceutically acceptable salts include normal nontoxic salts or quaternary ammonium salts of maternal compounds, such as nontoxic salts formed from inorganic or organic acids. Normal nontoxic salts include, but are not limited to, those salts derived from inorganic or organic acids, and the aforesaid inorganic or organic acids are selected from 2-acetoxy benzoic acid, 2-hydroxyl ethanesulfonic acid, acetic acid, ascorbic acid, benzenesulfonic acid, benzoic acid, bicarbonate radical, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxyl, hydroxy naphthalene, isethionic acid, lactic acid, lactose, dodecyl sulfonic acid, maleic acid, malic acid, mandelic acid, methanesulfonic acid, nitric acid, oxalic acid, dihydroxy naphthalene acid, pantothenic acid, phenylacetic acid, phosphoric acid, polygalactose aldehyde, propionic acid, salicylic acid, stearic acid, subacetic acid, succinic acid, sulfamic acid, sulfanilic acid, sulfuric acid, tannin, tartaric acid and p-methylbenzenesulfonic acid.

Pharmaceutically acceptable salts in this invention can be synthesized through conventional chemical methods with maternal compounds containing acid radical or alkaline base. In general, the preparation methods of these salts is that in water or organic solvents or the mixture of both, dissociated acidic or alkaline forms of these compounds react with stoichiometric proper acids or alkalis to give salts. In general, preferably, ether, ethyl acetate, ethanol, isopropanol or acetonitrile, and the like non-aqueous media.

Including forms of salts, compounds provided in this invention also exist forms of prodrugs. Prodrugs of compounds described herein are transferred into compounds in this invention easily through chemical reaction in physiological conditions. Besides, prodrugs can be transferred into compounds in this invention easily through chemical or biochemical methods in vivo environment.

Certain compounds in this invention can exist in non-solvent or solvent forms, including hydrate forms. In general, solvent forms are comparable to non-solvent forms, which are included in this invention.

Certain compounds in this invention can contain the asymmetric carbon (optical center) or double bond. Racemic mixtures, asymmetric isomers, geometric isomers, and single isomers are all included in this invention.

The diagram method of racemates, ambiscalemic and scalemic or enantiomer pure compounds comes from Machr, J. Chem. Ed. 1985, 62: 114-120. 1985, 62: 114-120. Unless otherwise stated, the wedge key and dashed key represent a stereocentric absolute configuration. When the aforesaid compounds in this article contain olefinic double bonds or other geometric asymmetry centers, unless otherwise stated, they include E, Z geometrical isomers. Similarly, all the tautomeric forms are included in this invention.

The compounds in this invention can exist specific geometrical or stereo isomer forms. This invention conceives all this kind compounds, which include cis- and trans-isomers, (−)- and (+)-enantiomers, (R)- and (S)-enantiomers, diastereomers, (D)-isomers, (L)-isomers, their racemic mixtures and other mixtures, such as the mixture rich in symmetric isomers and diastereomers, and all these mixtures are included in this invention. Substituents such as alkyl may exist other asymmetric carbon, and all these isomers and their mixture are included in this invention.

The optically active (R)- and (S)-enantiomers, and (D)- and (L)-isomers can be prepared through chiral synthesis, or chiral reagents or other conventional techniques. If a kind of enantiomers is needed in this invention, they can be prepared through asymmetric synthesis or derivatization of chiral auxiliary, where obtained mixtures of diastereomers are separated and then auxiliary groups are ruptured to give pure needed enantiomers. Or, when compounds contain alkaline groups (such as amino) or acidic groups (such as carboxyl), they form salts of diastereomers with appropriate optically active acids or alkalis which are splitted through conventional methods known in this field to give pure enantiomers. Besides, the separate of enantiomers and diastereomers is through chromatography, and the aforesaid chromatography uses chiral stationary phases, and combines with chemical derivatization optionally (such as amine forming carbamate).

Compounds in this invention can contain unnatural ratio atomic isotopes in one or multi-atoms forming compounds. For example, compounds can be labeled with radioactive isotopes, such as tritium ($^3$H), iodine-125 ($^{125}$I) or carbon-14 ($^{14}$C). The conversion of all the isotopes constituting compounds in this invention, whether radioactivity or not, are included in this invention.

The term "pharmaceutically acceptable carrier" means any preparation or supported media that can deliver effective amount of active substance in this invention, don't interfere biological active of active substance and is nontoxic to hosts or patients, and representative carriers include water, oil, vegetable and mineral, cream base, lotion base, ointment base and so on. These bases include suspending agent, tackifier and penetration enhancer and so on. Their preparations are known to technicians in cosmetic and topical medication fields. Other information about carriers, can refer to the literature Remington: The Science and Practice of Pharmacy, 21st ED., Loppincott, Williams & Wilkins (2005), and contents of this literature merge into this article by quoting.

The term "excipient" usually means carrier, diluent and/or media which are needed for preparation of effective pharmaceutical compositions.

In allusion to medicine or pharmacological activator, the term "effective amount" or "therapeutically effective amount" means enough amount of medicine or agent which can achieve the desired affect without toxin. For the oral preparation in this invention, "effective amount" of a kind of active substance in compositions means the amount needed to achieve the desired affect when combining with another active substance in compositions. The effective amount varies with each individual, and depends on ages of receptors and general situations, also specific active substances. In individual cases, appropriate effective amount can be determined according to routine tests by technicians in this field.

The term "active constituent", "therapeutic agents", "active substance" or "active agent" mean a kind of chemical entities which treat targeted disorders, diseases or symptoms.

The term "substituted", as used herein, means that any one or more hydrogens on the designated atom is replaced with a selection from the indicated group, including deuterium "D" atom, a variant hydrogen, provided that the designated atom's normal valency is not exceeded, and that the substitution results in a stable compound. When a substituent is keto (i.e., =O), then two hydrogens on the atom are replaced. Keto substituents are not present on aromatic moieties. The term "optionally substituted", as used herein, means that the designated atom can be substituted or unsubstituted by the substituents, and unless otherwise stated, the species and number of the substituents are not defined provided that they can be achieved in Chemistry.

When any variable (e.g. R) occurs more than one time in any constituents or formula for a compound, its definition at each occurrence is independent of its definition at every other occurrence. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When the number of a bonding group is zero, for example, —(CRR)$_0$—, then this bonding group is a single bond.

When one of variants is selected from single bond, then two groups bonding by this variant are bonded directly, for example, when "L" in "A-L-Z" represents a single bond, this formula is "A-Z" actually.

When a substituent is vacant, then this substituent doesn't exist, for example, when "X" in "A-X" is vacant, this formula is "A" actually. When a bond to a substituent is shows to cross a bond connecting two atoms in a ring, then such substituent may be bonded to any atom on the ring. When a substituent is listed without indicating the atom via which such substituent is bonded to the rest of compound of a given formula, then such substituent may be bonded via any atom in such substituent. Combinations of substituents and/or variables are permissible only if such combinations result in stable compounds. For example, structural units

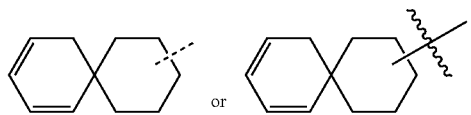

mean any site of cyclohexyl or cyclohexadiene can be substituted.

The terms "halo" or "halogen", by themselves or as a part of another substituent, mean, unless otherwise stated, a fluorine, chlorine, bromine, or iodine atom. Additionally, terms such as "haloalkyl", are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$ and $C_6$ alkoxy groups. Examples of alkoxy include, but are not limited to, methoxy, ethoxy, n-propoxy, i-propoxy, n-butoxy, s-butoxy, t-butoxy, n-pentoxy, and a-pentoxy. "Cycloalkyl" is intended to include saturated ring groups, such as cyclopropyl, cyclobutyl, or cyclopentyl. 3-7 cycloalkyl is intended to include hydrocarbon chains of either straight or branched configuration and one or more unsaturated carbon-carbon bonds that may occur in any stable point along the chain, such as ethenyl and propenyl.

"Halo" or "halogen" as used herein refers to fluoro, chilro, bromo, and iodo.

As used herein, the term "hetero", means, unless otherwise stated, "heteroatom" or "heteroradical" (namely radical containing heteroatom), including atoms other than carbon (C) and hydrogen (H), also including the radicals containing these aforesaid heteroatoms. Examples include oxygen (O), nitrogen (N), sulfur (S), silicon (Si), germanium (Ge), aluminum (Al), and boron (B), also include optically substituted —C(=O)N(H)—, —N(H)—, —C(=NH)—, —S(=O)$_2$N(H)—, or —S(=O)N(H)—.

"Ring" as used herein, means a substituted or unsubstituted cycloalkyl, heterocyclalkyl, cycloalkenyl, heterocycloalkenyl, cycloalkynyl, heterocycloalkybyl, aryl, or heteroaryl. A ring includes mono, bi, sprio, fused, and bridged ring moieties. The number of atoms in a ring is typically defined by the number of the members in the ring, For example, a "5- to 7-membered ring", means there are 5 to 7 atoms in the encircling arrangement. Unless otherwise specified, the ring optically includes one to three heteroatoms. Thus, the term "5- to 7-membered ring" includes, for example, phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heterocycle" or "heterocyclic group" is intended to mean a stable monocyclic, bicyclic, or tricyclic ring containing heteroatom or heteroradical, which is saturated, partially saturated or unsaturated (aromatic), and which consists of carbon atoms and 1, 2, 3, or 4 ring heteroatoms independently selected from the groups consisting of N, O and S and including any bicyclic groups in which any of the above-defined heterocyclic rings is fused to a benzene ring. The nitrogen and sulfur heteroatoms may optically be oxidized (i.e. NO and S(O)p, p is 1 or 2). The nitrogen atom may be substituted or unsubstituted (i.e. N or NR wherein R is H or another substituent, if define). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not more than 1. As used herein, the term "aromatic heterocyclic group" or "heteroaryl" is tended to mean a stable 5, 6, or 7-membered monocyclic or bicyclic or 7, 8, 9, or 10-membered bicyclic heterocyclic aromatic ring which consists of carbon atoms and 1, 2, 3 or 4 heteroatoms independently selected from the group consisting of N, O and S. The nitrogen atom may be substituted or unsubstituted (i.e. N or NR wherein R is H or another substituent, if defined). The nitrogen and sulfur heteroatoms may optionally be oxidized (i.e., NO and S(O)p, p is 1 or 2). It is to be noted that total number of S and O atoms in the aromatic heterocycle is not more than 1. Bridged rings are also included in the definition of heterocylce. A bridged ring occurs when one or more atoms (i.e., C, O, N, or S) link two non-adjacent carbon or nitrogen atoms. Preferred bridges include, but are not limited to, one carbon atom, two carbon atoms, one nitrogen, two nitrogen atoms, and a carbon-nitrogen group. It is noted that a bridge always converts a monocyclic ring into a tricyclic ring. When a ring is bridged, the substituents recited for the ring may also be present on the bridge.

Example of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, dihydrobenzofuran, chromenyl, decahydroquinolinyl, 2H,6H-1,5-2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indoliziny, indolyl, 3H-indolyl, isobenzofuranyl, isoindolinyl, isoindolyl, isoquinolinyl, isothiazolyl, isoxazolyl, methylenedioxyphenyl, morpholiny, naphthyridinyl, octahydroisoquinolinyl, oxadiazolyl, 1,2,3-oxadiazoyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, benzodiazepinyl, phenoloxazinyl phthalazinyl, piperazinyl, piperidinyl, piperidonyl, 4-piperidonyl, piperonyl, pteridinyl, purinyl, pyranyl, pyrazinyl, pyrazolidinyl, pyrodazinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroidoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthiophenyl, thienooxazolyl, thienothiazolyl, thienoimidazole, thienyl, triazinyl, 1,2,3-triazolyl, 1,2,4-triazolyl, 1,2,5-triazolyl, 1,3, 4-triazolyl, and xanthenyl. Also included are fused ring and spiro compounds.

The term "hydrocarbyl" or it lower concept (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). "hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl includes, but is not limited to, 6-12 membered aromatic hydrocarbyl, for example, benzene, and naphthalene. In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of, for example, n-pentyl, n-hexyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its lower concept (such as heteroalkyl, heteroalkeneyl, heteroalkynyl and heteroaryl etc.) by itself or in combination with another term, means, unless otherwise stated, a stable straight or branched chain, or cyclic hydrocarbon radical,or combinations thereof, consisting of the stated number of carbon atoms and at least one heteroatom. In some embodiments, the term "heteroalkyl", by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heterohydrocarbyl group (including the position at which the hydrocarbyl group is attached to the remainder of the molecule). Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —$CH_2$—$CH_2$—S (O)—$CH_3$, —$CH_2$—$CH_2$—S(O)$_2$—$CH_3$, —CH=CH— O=$CH_3$, —$CH_2$—CH=N—$OCH_3$, and —CH=CH—N ($CH_3$)—$CH_3$. Up to two heteroatoms may be consecutive, such as, for example, —$CH_2$—NH—$OCH_3$.

The term "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively.

The term "cyclohydrocarbyl", "heterocyclohydrocarbyl", or their lower concept (such as aryl, heteroaryl, cycloalkyl, heterocycloalkyl, cycloalkenyl, heterocycloalkenyl, cycloalkynyl, and heterocycloalkynyl etc.) by themselves or in combination with other terms mean cyclized hydrocarbyl and heterohydrocarbyl, respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl and 2-piperazinyl.

The term "aryl" means, unless otherwise stated, a polyunsaturated aromatic substituent that can be a single ring or multiple rings (preferably from 1 to 3 rings, one ring is aryl at less), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidy, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Unless otherwise stated, the term "aryl" when used in combination with other terms (e.g., aryloxy, arylthio, aralkyl) includes both aryl and heteroaryl rings as defined above. Thus, the term "aralkyl" is meant to include those radicals in which an aryl group is attached to an alkyl group (e.g., benzyl, phenethyl, pyridylmethyl and the like) including those alkyl group in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "leaving group" means a functional group or atom which can be displaced by another functional group or atom in a substitution reaction, such as a nucleophilic substitution reaction. By way of example, representative leaving groups include triflate, chloro, bromo and iodo group; sulfobic ester groups, such as mesylate, tosylate, brosylate, nosylate and the like; and acyloxy groups, such as acetoxy, trifluoroacetoxy and the like.

The term "protecting group" includes but is not limited to "amino-protecting group", "hydroxyl-protecting group" and "thiol-protecting group". The term "amino-protecting group" means a protecting group suitable for preventing undesired reactions at an amino nitrogen. Representative amino-protecting groups include, but are not limited to, formyl; acyl group, for example alkanoyl groups, such as acetyl, trichloroacetul or trifluoroacetyl; alkoxycarbonyl groups, such as tert-butoxycarbonyl (Boc); arylmethoxycarbonyl groups, such as benzyloxycarbobyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butylsimethylsilyl (TBS); and the like. The term "hydroxyl-protecting group" means a protecting group suitable for preventing undesired reactions at a hydroxyl group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butylsimethylsilyl (TBS); and the like.

The compounds of this invention can be prepared in a number of ways known to one skilled in the art of organic synthesis. The examples of this invention can be synthesized using the methods described below, together with synthetic methods known in the art of synthetic organic chemistry, or by variations thereon as appreciated by those skilled in the art. Concrete methods include, but are not limited to, those describe below.

All solvents used are commercially available. This present invention adopts following abbreviating words: aq means aqueous; HATU means 2-(7-Azabenzotriazol-1-yl)-N,N,N',N'-tetramethyluroniumhexafluorophosphate; EDC means N-(3-Dimethylaminopropyl)-N'-ethylcarbodiimide hydrochloride; m-CPBA means 3-chloroperoxybenzoic acid; eq means equivalent; CDI means carbonyldiimidazole; DCM means dichloromethane; PE means petroleum ether; DIAD means diisopropyl azodiformate; DMF means N,N-dimethylformamide; DMSO means dimethyl sulfoxide; EtOAc means ethyl acetate; EtOH means ethanol; MeOH means methanol; CBz means carbobenzyloxy, a kind of protecting group for amine; BOC means t-butyloxy carbonyl, a kind of protecting group for amine; HOAc means acetic acid; NaCNBH$_3$ means sodium cyanoborohydride; r.t. means room temperature; O/N means overnight; THF means tetrahydrofuran; Boc$_2$O means di-tert-butyl dicarbonate; TFA means trifluoroacetic acid; DIPEA means ethyldiisopropylamine; SOCl$_2$ means thionyl chloride; CS$_2$ means carbon disulfide; TsOH means p-toluenesulfonic acid; NFSI means N-Fluorobenzenesulfonimide; NCS means N-Chlorosuccinimide; n-Bu$_4$NF means tetrabutylammonium fluoride; iPrOH means 2-propanol; mp means melting point; LDA means lithium diisopropylamide.

Compounds are named either manually or by using ChemDraw®, or using vendors catalogue name if commercially available.

DETAILED DESCRIPTION OF THE PREFERRED EMBODIMENT

Figure 1:
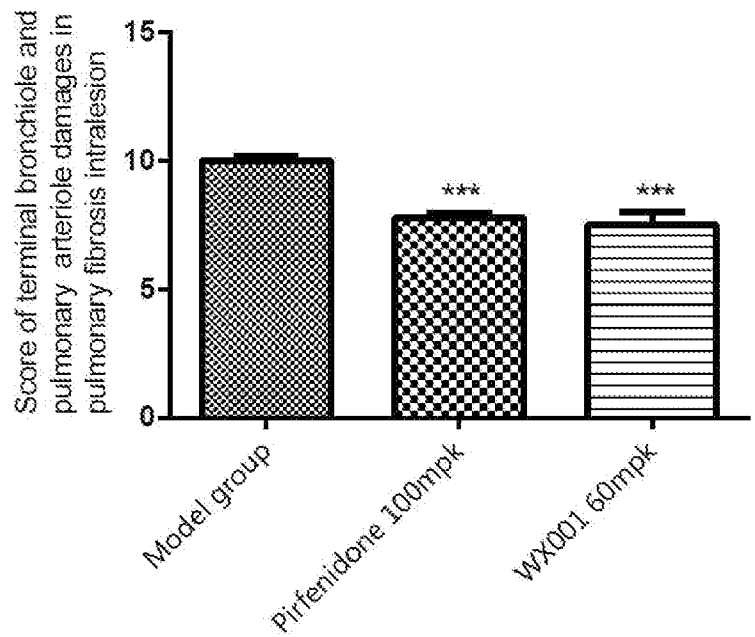
FIG. 1 is grade of WX001 improving tissue damage in the area of pulmonary fibrosis

The present invention will be specifically described below by way of embodiments, but the scope of the present invention is not limited thereto. The present invention has been described in detail and the embodiments are disclosed as well, any modification of the embodiment without departing from the spirit of the present invention should be considered obviousness.

Reference Embodiment 1: Intermediate A-1

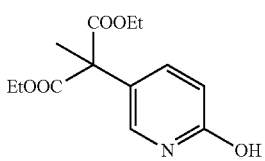

Synthetic Route:

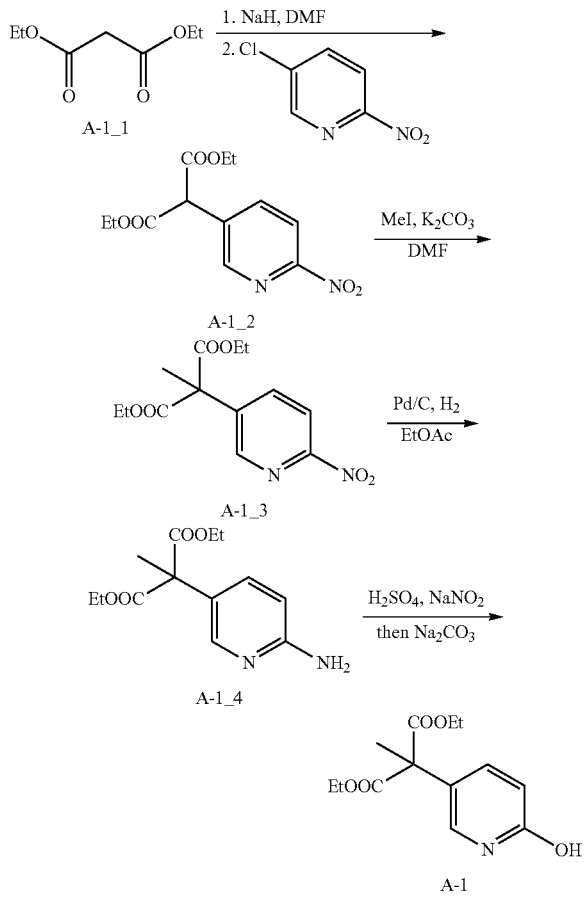

Step 1: Synthesis of Compound A-1_2

To a suspension of NaH (1.99 g, 49.83 mmol) in anhydrous DMF (75 mL) at 10° C. under $N_2$ atmosphere, was added diethyl malonate (6.57 g, 41.00 mL) dropwise. After addition, the mixture was stirred for 0.5 h at room temperature, and then 5-chloro-2-nitropyridine (5.00 g, 31.54 mmol) was added in anhydrous DMF (25 mL) dropwise. The mixture was warmed to 80° C. slowly and stirred for another 12 h. After the reaction finished, the mixture was quenched with water (2300 mL), and then extracted with EtOAc (500 mL*4). The combined organic phase was washed with sat. aq NaCl (100 mL), dried over $Na_2SO_4$, filtered and concentrated in vacuo. The residue was purified by flash column chromatography eluted with Pet. Ether/EtOAc (10/1 to 5/1) to give compound A-1_2 as tangerine solid (5.40 g, 60.66%). $^1$H NMR (400 MHz, $CDCl_3$) δ: 8.63 (d, J=2.0 Hz, 1H), 8.33-8.28 (m,1H), 8.26 (d, J=2.0 Hz, 1H), 4.81 (s, 1H), 4.33-4.21 (m, 4H), 1.33-1.28 (m, 6H).

Step 2: Synthesis of Compound A-1_3

To a solution of compound A-1_2 (5.00 g, 17.71 mmol) in anhydrous DMF (50 mL) at room temperature was added potassium carbonate (4.90 g, 35.42 mmol) and then added methyl iodide (5.03 g, 35.42 mmol) dropwise. The mixture was stirring for 1 h at 25° C. After the reaction finished, the mixture was diluted with water (900 mL) and extracted with EtOAc (200 mL*3). The combined organic phase was washed with sat. aq NaCl (50 mL), dried over $Na_2SO_4$, filtered and concentrated in vacuo. The residue was purified by flash column chromatography eluted with Pet. Ether/EtOAc (10/1) to give compound A-1_3 as yellow solid (5.25 g, 100%). $^1$H NMR (400 MHz, $CDCl_3$) δ: 8.67 (d, J=2.0 Hz, 1H), 8.25 (d, J=8.5 Hz, 1H), 8.10 (dd, J=2.5, 8.5 Hz, 1H), 4.27 (dq, J=2.0, 7.1 Hz, 4H), 1.94 (s, 3H), 1.28 (t, J=7.0 Hz, 6H).

Step 3: Synthesis of Compound A-1_4

To a solution of compound A-1_3 (17.00 g, 60.23 mmol) in EtOAc (150 mL) at room temperature was added 10% wet Pd/C (3.20 g, 3.01 mmol) and the mixture was stirring for 12 h at 40° C. under the atmosphere of 50 psi $H_2$. After the reaction finished, the mixture was filtered and the catalyst was washed with EtOAc (20 mL*3). The filtrate was concentrated in vacuo to give compound A-1_4 as tangerine solid (13.70 g, 85.42%) used for next synthesis without further purification. $^1$H NMR (400 MHz, $CDCl_3$) δ: 7.83 (d, J=2.5 Hz, 1H), 7.34 (dd, J=2.5, 8.8 Hz, 1H), 6.45-6.39 (m, 1H), 5.99 (s, 2H), 4.15 (q, J=7.0 Hz, 4H), 1.74-1.66 (m, 3H), 1.17 (t, J=7.0 Hz, 6H).

Step 4: Synthesis of Compound A-1

At room temperature, compound A-1_4 (13.70 g, 51.45 mmol) was dissolved in 70% aq. $H_2SO_4$ (92.00g, 50 mL), the mixture was cooled to −5° C. and aqueous sodium nitrite (4.30 g, 62.25 mmol) solution (3.5 ml) was added dropwise while the inner temperature maintained under 0° C. The mixture was stirred for 0.5 h at −5° C. and then warmed to room temperature, and stirred for another 3 h. After the reaction finished, the mixture was deluted with water (800 mL), adjusted pH to 9-10 with sat. aq $Na_2CO_3$ and then extracted with EtOAc (200 mL*4). The combined organic phase was washed with sat. aq. NaCl (50 mL), dried over anhydrous $Na_2SO_4$, desiccant was filtered and concentrated in vacuo. The residue was purified by flash column chromatography eluted with Pet. Ether/EtOAc (5/1 to pure EtOAc) to give compound A-1 as brown solid (11.00 g, 80%). $^1$H NMR (400 MHz, $CDCl_3$) δ: 12.88 (br.s. 1H), 7.60 (dd, J=2.8, 9.8 Hz, 1H), 7.38 (d, J=3.0 Hz, 1H), 6.57 (d, J=9.5 Hz, 1H), 4.23 (q, J=6.9 Hz, 4H), 1.76 (s, 3H), 1.26 (t, J=7.0 Hz, 6H).

Reference Embodiment 2: Intermediate B-1

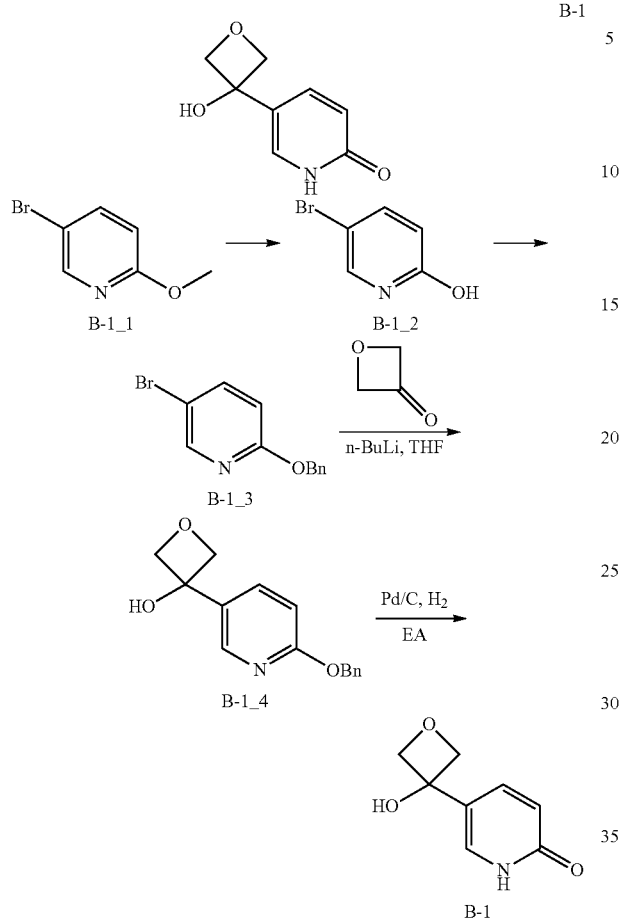

Step 1: Synthesis of Compound B-1_2

The mixture of 5-bromo-2-methoxypyridine (15.00 g, 79.78 mmol) and diluted hydrochloric acid (6M, 150 mL) was stirred for 20 h at 100° C. After the reaction finished, the mixture was diluted with water (600 mL), adjusted pH to 7 with aq. NaOH solution (1M), and then extracted with EtOAc (200 mL*4). The combined organic phase was washed with sat. aq NaCl (20 mL), dried over Na$_2$SO$_4$, filtered and concentrated in vacuo. The residue was mashed with mixed solvents (PE/EtOAc =10/1, 100 mL), filtered and then washed with PE (5 mL*3), dried in vacuo to give compound B-1_2 as white solid (10.42 g, 61.55%). $^1$H NMR (400 MHz, CDCl$_3$) δ: 11.76 (br.s., 1H), 7.70 (d, J=3.0 Hz, 1H), 7.56 (dd, J=2.5, 9.5 Hz, 1H), 6.36 (d, J=9.5 Hz, 1H).

Step 2: Synthesis of Compound B-1_3

To a solution of compound B-1_2 (10.40 g, 59.77 mmol) in anhydrous toluene (400 mL) at room temperature under N$_2$ was added silver carbonate (24.72 g, 89.66 mmol) and benzyl bromide (10.22 g, 59.77 mmol), and the mixture was stirred for 20 h at 110° C. After the reaction finished, the mixture was filtered with kieselguhr, the filter cake was washed with dichloromethane (20 mL*5), and the filtrate was concentrated in vacuo. The residue was purified by flash column chromatography eluted with Pet. Ether/EtOAc (10/1) to give compound B-1_3 as white solid (15.00 g, 95%). $^1$H NMR (400 MHz, CDCl$_3$) δ: 8.22 (d, J=2.0 Hz, 1H), 7.66 (dd, J=2.5, 8.5 Hz, 1H), 7.48-7.42 (m, 2H), 7.39 (br.t., J=7.3 Hz, 2H), 7.34 (br.d., J=7.0 Hz, 1H), 6.73 (d, J=8.5 Hz, 1H), 5.35 (s, 2H).

Step 3: Synthesis of Compound B-1_4

To a solution of compound B-1_3 (2.00 g, 7.57 mmol) in anhydrous THF (20 mL) at −70° C. under N$_2$ was added 2.5M n-butyllithium (3.21 mL, 8.02 mmol) solution dropwise to give yellow suspension, and then the mixture was stirred for 0.5 h at −70° C. and then oxetanone (0.60 g, 8.33 mmol) in THF (6 mL) was added dropwise at the same temperature. The mixture was stirred for 1 h at −70° C. After the reaction finished, the mixture was quenched with sat. aq. NH$_4$Cl (5 mL), diluted with water (50 mL), extracted with EtOAc (30 mL*3). The combined organic phase was washed with sat. aq. NaCl (10 mL), dried over anhydrous Na$_2$SO$_4$, the drier was filtered out and the solution was concentrated in vacuo. The residue was purified by flash column chromatography eluted with Pet. Ether/EtOAc (10/1 to 1/1) to give compound B-1_4 as white solid (1.80 g, 92.42%). $^1$H NMR (400 MHz, CDCl$_3$) δ: 8.40 (d, J=2.5 Hz, 1H), 7.83 (dd, J=2.5, 8.5 Hz, 1H), 7.49-7.44 (m, 2H), 7.41-7.36 (m, 2H), 7.35-7.31 (m, 1H), 6.87 (d, J=8.5 Hz, 1H), 5.40 (s, 2H), 4.92-4.88 (m, 4H), 2.60 (br.s., 1H).

Step 4: Synthesis of Compound B-1

Compound B-1_4 (1.40 g, 5.44 mmol) was dissolved in EtOAc (30 mL) at room temperature, 10% wet Pd/C (580 mg, 544 μmol) was added and the mixture was stirring for 1 h at 25° C. under the atmosphere of 15 psi H$_2$. After the reaction finished, the mixture was filtered and the catalyst was washed with a mixed solvent of DCM/MeOH (10:1, 50 mL*3). The filtrate was concentrated in vacuo to give compound B-1 as white solid (800.00 mg, 87.97%) which can be used for next synthesis without further purification. $^1$H NMR (400 MHz, CDCl$_3$) δ: 7.71 (dd, J=2.8, 9.3 Hz, 1H), 7.43 (d, J=2.5 Hz, 1H), 6.45 (d, J=9.5 Hz, 1H), 4.74-4.70 (m, 2H), 4.69-4.65 (m, 2H).

Reference Embodiment 3: Intermediate C-1

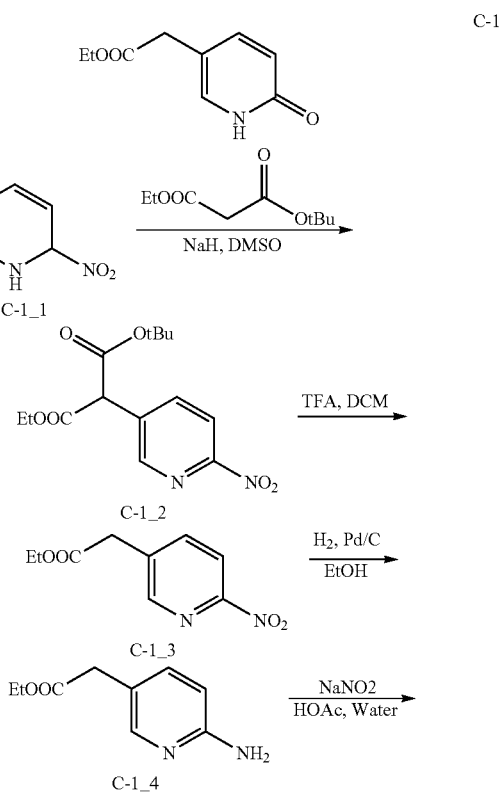

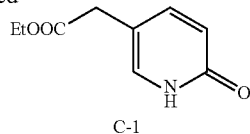

Step 1: Synthesis of Compound C-1_2

To a solution of tert-butyl ethyl malonate (46.36 g, 246.31 mmol) in DMSO (125 mL) at 10° C. under $N_2$ was added 60% NaH (9.85 g, 246.31 mmol). The mixture was warmed to 15° C. and stirred for 0.5 h, and then 5-bromo-2-nitropyridine (25.00 g, 123.16 mmol) was added dropwise. The mixture was warmed to 80° C. and stirred for another 5 h. After TLC detected that the reaction finished, the mixture was quenched with sat. aq $NH_4Cl$ (150 mL), and then extracted with EtOAc (200 mL). The organic phase was washed with water (150 mL) and sat. aq. NaCl (150 mL), dried over $Na_2SO_4$, the drier was filtered out and the solution was concentrated in vacuo to give the residue C-1_2 (65 g) as yellow oil without further purification and used for next step.

Step 2: Synthesis of Compound C-1_3

To a solution of compound C-1_2 (65.00 g, 209.47 mmol) in anhydrous DCM (200 mL) at room temperature was added trifluoroacetic acid (200 mL, 2.70 mol) and the mixture was stirred for 1.5 h at 40° C. After TLC detected that the reaction finished, the mixture was concentrated to dry in vacuo. The residue was dissolved in EtOAc (200 mL) and washed with sat. aq $NaHCO_3$ (150 mL) and sat. aq NaCl (150 mL). The organic phase was dried over $Na_2SO_4$, the drier was filtered out and the filtrate was concentrated in vacuo. The residue was purified by flash column chromatography eluted with Pet. Ether/EtOAc (10/1 to 3/1) to give compound C-1_3 as white solid (16.70 g, 96.42%). $^1H$ NMR (400 MHz, $CDCl_3$) δ: 8.56 (d, J=2.13 Hz, 1H), 8.26 (d, J=8.28 Hz, 1H), 8.01 (dd, J=8.34, 2.20 Hz, 1H), 4.21 (q, J=7.07 Hz, 2H), 3.79 (s, 2H), 1.29 (t, J=7.09 Hz, 3H).

Step 3: Synthesis of Compound C-1_4

To a solution of compound C-1_3 (15.60 g, 74.22 mmol) in EtOH (150 mL) at room temperature was added 10% Pd/C (1.56 g) and the mixture was stirring for 11.5 h at 15° C. under the atmosphere of 15 psi $H_2$. After LCMS showed that the reaction finished, the mixture was filtered and the filtrate was concentrated to dry in vacuo to give compound C-1_4 as mahogany oil (13.05 g, 96.98%) used for next synthesis without further purification. $^1H$ NMR (400 MHz, $CDCl_3$) δ: 7.77 (d, J=1.96 Hz, 1H), 7.26 (dd, J=8.44, 2.45 Hz, 1H), 6.40 (d, J=8.44 Hz, 1H), 5.82 (s, 2H), 4.06 (q, J=7.13 Hz, 2H), 3.44 (s, 2H), 2.41-2.59 (m, 4H), 1.18 (t, J=7.09 Hz, 3H).

Step 4: Synthesis of Compound C-1

To a solution of compound C-1_4 (10.00 g, 55.49 mmol) in acetic acid (625 mL) was added aqueous sodium nitrite (16.46 g, 238.62 mmol) solution (18.75 ml) in 10 min at 80° C. The mixture was stirred for 0.5 h at 80° C., water (50 mL) was added and then the mixture was stirred for another 2 h. After LCMS showed the reaction finished, the mixture was concentrated in vacuo. The residue was dissolved in EtOAc (100 mL) and then filtered, the filter cake was washed with small amount of EtOAc until it became white solid, the filtrate was concentrated to dry under reduced pressure. The residue was dissolved with EtOAc again, this operation was repeated for several times to remove inorganic salts in crude product. The crude product was dissolved with EtOAc (100 mL) and aqueous phase was adjusted to neutral (pH=7-8) with saturated aq. $NaHCO_3$. The organic phase was dried over $Na_2SO_4$, filtered and concentrated in vacuo. The residue was dissolved with EtOAc (20 mL), filtered to remove the insolubles and give compound C-1 as yellow solid (7.50 g, 74.59%). $^1H$ NMR (400 MHz, $CDCl_3$) δ: 11.47 (br.s., 1H), 7.34 (dd, J=9.29, 2.64 Hz, 1H), 7.26 (d, J=2.13 Hz, 1H), 6.30 (d, J=9.41 Hz, 1H) 4.08 (q, J=7.15 Hz, 2H), 3.43 (s, 2H), 1.19 (t, J=7.09 Hz, 3H).

Embodiment 1 WX001

Synthetic Scheme:

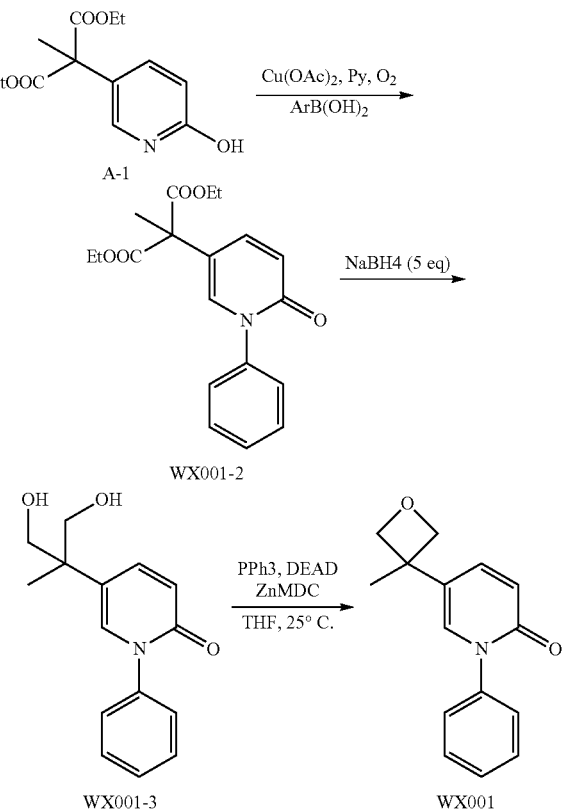

Step 1: Synthesis of Compound WX001-2

To a solution of compound A-1 (10.90 g, 40.78 mmol) and phenylboronic acid (5.02 g, 41.19 mmol) in anhydrous DCM (130 mL) at room temperature under $O_2$ was added copper acetate (7.41 g, 40.78 mmol), triethylamine (8.25 g, 81.56 mmol) and powdery 4 A molecular sieve (2.20 g), and the mixture was stirred for 12 h at room temperature. After the reaction finished, the mixture was filtered and the solid was washed with DCM (100 mL*4). The filtrate was combined and concentrated in vacuo. The residue was purified by flash column chromatography eluted with Pet. Ether/EtOAc (from 10:1 to 1:1) to give compound WX001-2 as yellow solid (13.00 g, 92.84%). $^1$H NMR (400 MHz, CDCl$_3$) δ: 7.55-7.47 (m, 3H), 7.44 (d, J=7.5 Hz, 1H), 7.39 (d, J=7.5 Hz, 2H), 7.35 (d, J=2.5 Hz, 1H), 6.65 (d, J=9.5 Hz, 1H), 4.25(q, J=7.0 Hz, 4H), 1.76 (s, 3H), 1.28 (t, J=7.0 Hz, 6H).

Step 2: Synthesis of Compound WX001-3

To a solution of compound WX001-2 (10.00 g, 29.12 mmol) in MeOH (150 mL) at 0° C. under N$_2$ was added NaBH$_4$ (5.51 g, 145.60 mmol) in batches, and the mixture was warmed to 25° C. slowly, and stirred for 12 h at 25° C. The mixture was poured into DCM (1500 mL), and stirred for 1 h at room temperature. The mixture was filtered to remove the insoluble and concentrated to dry in vacuo. The residue was purified by flash column chromatography eluted with DCM/MeOH (50/1 to 10/1) to give compound WX001-3 as white powder (3.00 g, 39.73%). $^1$H NMR (400 MHz, CDCl$_3$) δ: 7.55 (dd, J=2.8, 9.5 Hz, 1H), 7.50-7.38 (m, 4H), 7.35 (d, J=7.3 Hz, 2H), 6.60 (d, J=9.5 Hz, 1H), 3.71 (q, J=11.3 Hz, 4H), 1.10 (s, 3H).

Step 3: Synthesis of Compound WX001

To a solution of compound WX001-3 (500.00 mg, 1.93 mmol), triphenylphosphine (1.01 g, 3.86 mmol) and ziram (900 mg, 2.94 mmol) in anhydrous THF (15 mL) was added DEAD (672.00 mg, 3.86 mmol) dropwise at room temperature under N$_2$ and the mixture was stirred for 20 h at 30° C. After the reaction finished, the mixture was added with MeOH (50 mL), filtered to remove the insoluble and the filter cake was washed with MeOH (50 mL*2). The filtrate was combined and concentrated in vacuo. The residue was purified by flash column chromatography eluted with Pet. Ether/EtOAc (from 10:1 to pure EtOAc) to give compound WX001 (280.00 mg, 60.13%). $^1$H NMR (400 MHz, CDCl$_3$) δ: 7.59 (dd, J=2.6, 9.7 Hz, 1H), 7.54-7.47 (m, 2H), 7.47-7.41 (m, 1H), 7.38 (d, J=7.3 Hz, 2H), 7.14 (d, J=2.8 Hz, 1H), 6.74 (d, J=9.5 Hz, 1H), 4.80 (d, J=5.8 Hz, 2H), 4.61 (d, J=5.8 Hz, 2H), 1.67 (s, 3H).

Embodiment 2 WX002

Synthetic Scheme:

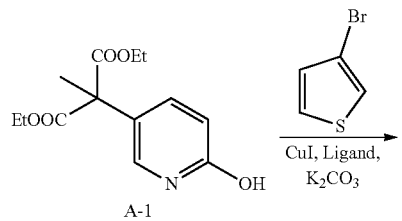

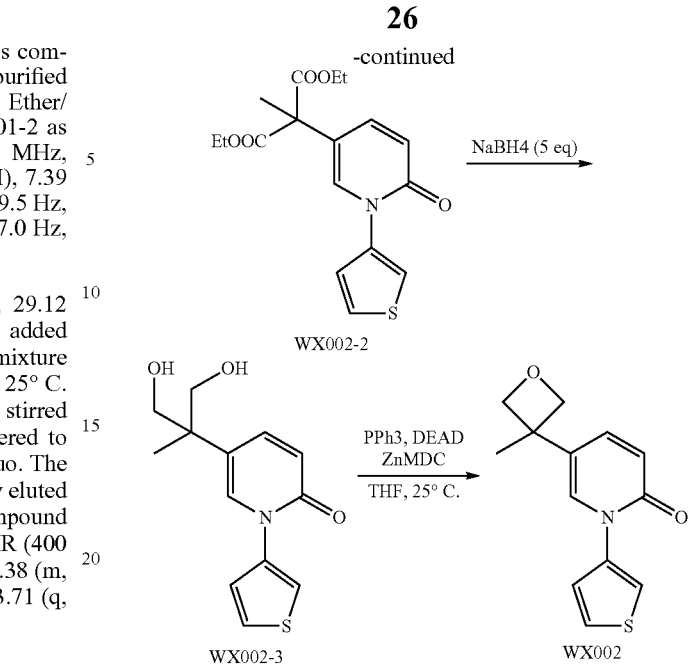

Step 1: Synthesis of Compound WX002-2

To a solution of compound A-1 (500.00 mg, 1.87 mmol) and 3-bromo-thiophene (304.88 mg, 1.87 mmol) in anhydrous dioxane (12 mL) was added cuprous iodide (356.14 mg, 1.87 mmol), N,N'-dimethyl-trans-cyclohexanediamine (427.07 mg, 3.74 mmol) and potassium carbonate (516.91 mg, 3.74 mmol) at room temperature under N$_2$, and the mixture was stirred for 12 h at 100° C. After the reaction finished, the mixture was diluted with water (50 mL), extracted with EtOAc (50 mL). The organic phase was washed with 5% ammonium hydroxide (20 mL*3) until the organic phase was luminous yellow and the water phase was not blue. And the water phase was extracted with EtOAc (30 mL*2) again. The organic phases were combined and concentrated to dry in vacuo. The residue was purified by flash column chromatography eluted with Pet. Ether/EtOAc (from 10/1 to 3/1) to give compound WX002-2 as yellow solid (550.00 mg, 84.18%). $^1$H NMR (400 MHz, CDCl$_3$) δ: 7.49 (dd, J=2.6, 9.7 Hz, 1H), 7.44-7.37 (m, 3H), 7.25 (br.d., J=5.3 Hz, 1H), 6.63 (d, J=9.8 Hz, 1H), 4.25 (q, J=7.2 Hz, 4H), 1.77 (s, 3H), 1.28 (t, J=7.2 Hz, 6H).

Step 2: Synthesis of Compound WX002-3

To a solution of compound WX002-2 (2.95 g, 8.44 mmol) in MeOH (45 mL) was added NaBH$_4$ (1.60 g, 42.20 mmol) in batches at 0° C. under N$_2$, and the mixture was warmed to 25° C. slowly, and stirred for 12 h. The mixture was poured into DCM (450 mL), and stirred for 1 h at room temperature. The mixture was filtered to remove insoluble and concentrated in vacuo. The residue was purified by flash column chromatography eluted with DCM/MeOH (50/1 to 10/1) to give compound WX002-3 as white powder (950.00 mg, 42.42%). $^1$H NMR (400 MHz, DMSO-d$_6$) δ: 7.76-7.72 (m, 1H), 7.67-7.58 (m, 2H), 7.42 (d, J=2.5 Hz, 1H), 7.31-7.27 (m, 1H), 6.45 (d, J=9.5 Hz, 1H), 4.65 (br.s., 2H), 3.56-3.49 (m, 2H), 3.48-3.42 (m, 2H), 1.11 (s, 3H).

Step 3: Synthesis of Compound WX002

To a solution of compound WX002-3 (900.00 mg, 3.39 mmol), triphenylphosphine (1.78 g, 6.78 mmol) and ziram (1.60 g, 5.22 mmol) in anhydrous THF (25 mL) was added DEAD (1.18 g, 6.78 mmol) dropwise at room temperature under N$_2$ and the mixture was stirred for 20 h at 30° C. After the reaction finished, the mixture was added with MeOH (50 mL), filtered and the solid was washed with MeOH (10 mL*2). The filtrate was combined and concentrated in vacuo. The residue was purified by flash column chromatography eluted with Pet. Ether/EtOAc (from 10:1 to pure EtOAc) to give yellow crude product containing little triphenylphosphine. The crude product was mashed with Pet. Ether/EtOAc (1:1, 10 mL) for 1 hr. and then filtered to collect solid. The filter cake was washed with Pet. Ether (5 mL*2) and the solid was dried in vacuo to give compound WX002 (280.00 mg, 87.50%). $^1$H NMR (400 MHz, CDCl$_3$) δ: 7.60 (dd, J=2.5, 9.5 Hz, 1H), 7.46-7.39 (m, 2H), 7.27-7.22 (m, 2H), 6.78 (d, J=9.5 Hz, 1H), 4.80 (d, J=6.0 Hz, 2H), 4.63 (d, J=5.8 Hz, 2H), 1.72-1.65 (m, 1H), 1.69 (s, 2H).

Embodiments listed below were synthesized according to the synthesis route of WX002

TABLE 1

| Embodiment | Fragment 1 | Fragment 2 | Structure | Compound |
|---|---|---|---|---|
| 3 | | | 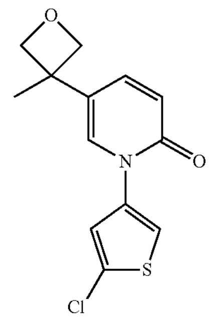 [SMILES: CC1(c2ccc(=O)n(-c3csc(Cl)c3)c2)COC1] | WX003 |
| 4 | | | 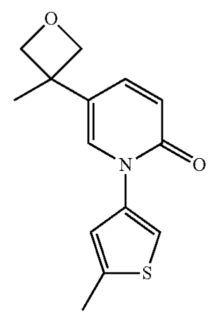 [SMILES: Cc1cc(-n2cc(C3(C)COC3)ccc2=O)cs1] | WX004 |
| 5 | | | 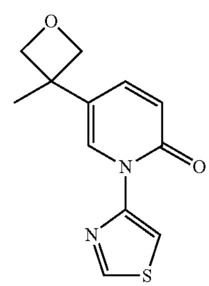 [SMILES: CC1(c2ccc(=O)n(-c3cscn3)c2)COC1] | WX005 |
| 6 | | | 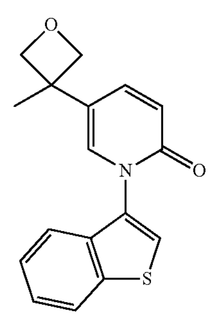 [SMILES: CC1(c2ccc(=O)n(-c3csc4ccccc34)c2)COC1] | WX006 |

TABLE 1-continued

| Embodiment | Fragment 1 | Fragment 2 | Structure | Compound |
|---|---|---|---|---|
| 7 | 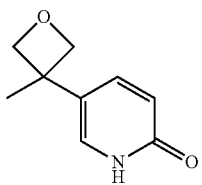 | 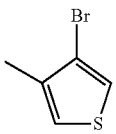 | 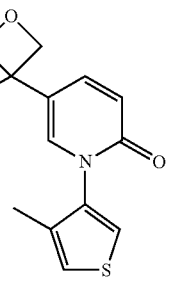 | WX007 |

Embodiment 8 WX008

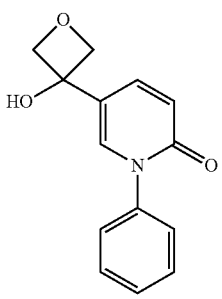

WX008

Synthetic Scheme:

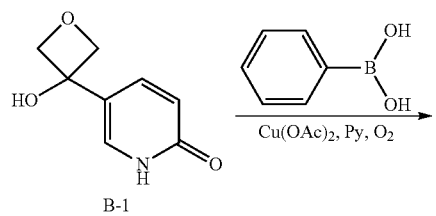

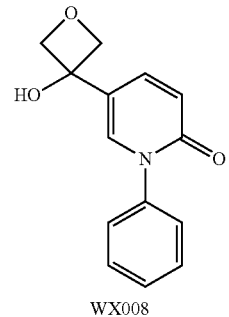

WX008

Step 1: Synthesis of Compound WX008

To a solution of compound B-1 (400.00 mg, 2.39 mmol) and phenyl boronic acid (300.00 mg, 2.46 mmol) in anhydrous DCM (20 mL) was added copper acetate (434.10 mg, 2.39 mmol), triethylamine (483.69 g, 4.78 mmol) and powdery 4 A molecular sieve (200.00 mg) at room temperature under $O_2$, and the mixture was stirred for 16 h at 30° C. After the reaction finished, the mixture was filtered to remove the insoluble and the solid was washed with DCM (30 mL*3). The filtrate was combined and concentrated in vacuo. The residue was purified by flash column chromatography eluted with Pet. Ether/EtOAc (from 5:1 to pure EtOAc) to give compound WX008 (420.00 mg, 72.24%). $^1$H NMR (400 MHz, CDCl$_3$) δ: 7.79 (dd, J=2.5, 9.5 Hz, 1H), 7.55 (d, J=2.5 Hz, 1H), 7.50-7.39 (m, 3H), 7.33 (d, J=7.0 Hz, 2H), 6.73 (d, J=9.5 Hz, 1H), 4.84 (d, J=7.3 Hz, 2H), 4.74 (d, J=7.3 Hz, 2H).

Embodiment 9 WX009

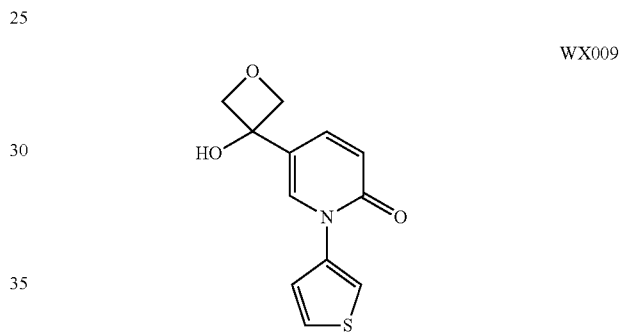

WX009

Synthetic Scheme:

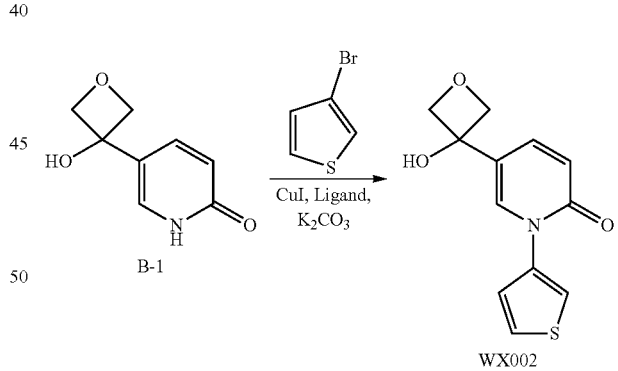

Step 1: Synthesis of Compound WX009

To a solution of compound B-1 (400.00 mg, 2.39 mmol) and 3-bromo-thiophene (401.36 mg, 2.46 mmol) in anhydrous dioxane (20 mL) was added cuprous iodide (455.18 mg, 2.39 mmol), N,N'-dimethyl-trans-cyclohexanediamine (545.83 mg, 4.78 mmol) and potassium carbonate (660.64 mg, 4.78 mmol) at room temperature under $N_2$, and the mixture was stirred for 16 h at 100° C. After the reaction finished, the mixture was filtered while hot, and the filter cake was washed with EtOAc (30 mL*3). The organic phase was washed with 5% ammonium hydroxide (20 mL*3) until the organic phase was luminous yellow and the water phase was not blue. And the water phase was extracted with EtOAc (20 mL*3) again. The organic phase was combined and concentrated to dry in vacuo. The residue was purified by flash column chromatography eluted with Pet. Ether/EtOAc (from 5/1 to pure EtOAc) to give compound WX009 (520.00 mg, 87.28%). $^1$H NMR (400 MHz, CDCl3) δ: 7.78 (dd, J=2.6, 9.4 Hz, 1H), 7.61 (d, J=2.3 Hz, 1H), 7.39-7.32 (m, 2H), 7.16 (dd, J=1.4, 5.1 Hz, 1H), 6.69 (d, J=9.3 Hz, 1H), 4.82 (d, J=7.3 Hz, 2H), 4.67 (d, J=7.3 Hz, 2H).

(180.00 mg, 89.26%). $^1$H NMR (400 MHz, CDCl$_3$) δ: 7.50 (dd, J=2.3, 9.5 Hz, 1H), 7.45-7.32 (m, 4H), 7.29 (d, J=7.0 Hz, 2H), 6.66 (d, J=9.5 Hz, 1H), 5.00-4.89 (m, 2H), 4.78-4.67 (m, 2H).

Embodiment listed below was synthesized according to the synthesis route of WX010

TABLE 2

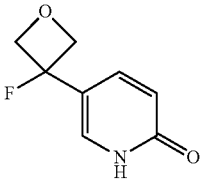 [SMILES: O=c1ccc(C2(F)COC2)c[nH]1]

Embodiment 10 WX010

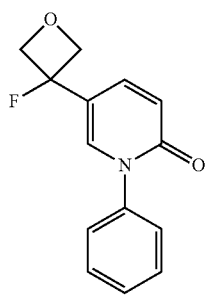

WX010

Synthetic Scheme:

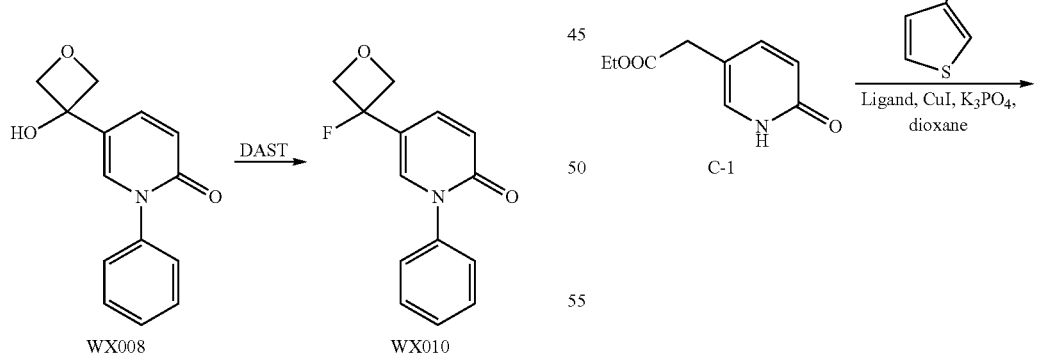

WX008     WX010

Step 1: Synthesis of Compound WX010

To a solution of compound WX008 (200.00 mg, 822.17 μmol) in anhydrous DCM (5 mL) was added DAST (245.82 mg, 1.51 mmol) at 0° C. under N$_2$, and the mixture was stirred for 2 h at 0° C. After the reaction finished, the mixture was poured into ice water to quench the reaction, and the mixture was extracted with DCM (20 mL*3). The organic phase was combined and concentrated in vacuo. The residue was purified by prep TLC to give compound WX010

Embodiment 12 WX012

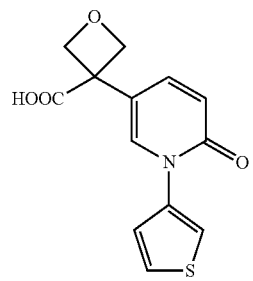

WX012

Synthetic Scheme:

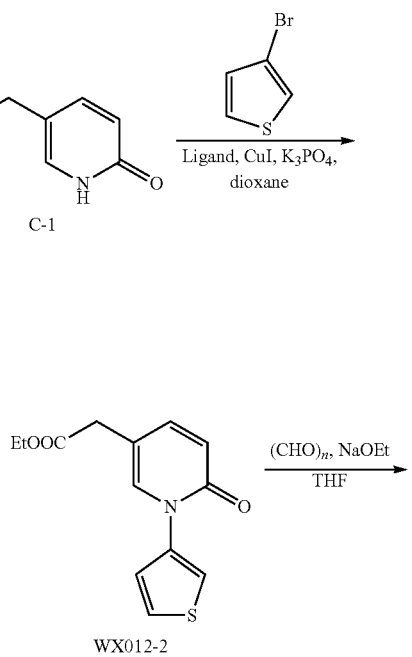

WX012-2

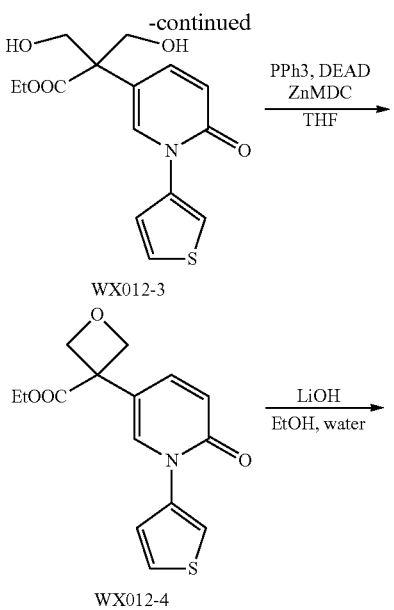

WX012-3

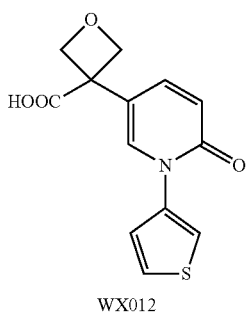

WX012-4

[Structure of WX012]

Step 1: Synthesis of Compound WX012-2

To a solution of compound C-1 (2.00 g, 11.04 mmol) and 3-bromo-thiophene (1.98 g, 12.14 mmol) in anhydrous dioxane (50 mL) was added cuprous iodide (2.10 g, 11.04 mmol), N,N'-dimethyl-trans-cyclohexanediamine (2.92 g, 33.11 mmol) and potassium phosphate (3.51 g, 16.56 mmol) at room temperature under $N_2$, and the mixture was stirred for 4 h at 110° C. After TLC showed the reaction finished, the mixture was filtered while hot, and the filtrate was concentrated to dry in vacuo. The residue was purified by flash column chromatography eluted with Pet. Ether/EtOAc (4:1 to 1:4) to give compound WX012-2 as yellow oil (2.65 mg, 90.51%). $^1$H NMR (400 MHz, CDCl3) δ: 7.75 (br.s., 1H) 7.66 (br.s., 2H) 7.43 (br.d., J=9.29 Hz, 1H) 7.29 (br.d., J=4.65 Hz, 1H) 6.48 (br.d., J=9.29 Hz, 1H) 4.10 (q, J=7.05 Hz, 2H) 3.51 (s, 2 H) 1.20 (br.t., J=6.97 Hz, 3H).

Step 2: Synthesis of Compound WX012-3

To a solution of sodium ethoxide (56.86 mg, 835.51 μmol) and paraformaldehyde (1.13 g, 12.53 mmol) in anhydrous THF (50 mL) was added compound WX012-2 (2.20 g, 8.36 mmol) in THF (20 mL) at −10° C., and the mixture was stirred for 4 h at 0° C. LCMS showed that the ingredient was not consumed completely, and the mixture was added with sodium ethoxide (56.86 mg, 835.51 μmol) in four batches, and the mixture was stirred for 40 h at 15° C. After TLC showed the reaction finished, the mixture was filtered to remove the insoluble and filtrate was concentrated to dry in vacuo. The residue was purified by prep HPLC (alkalinity) to give compound WX012-3 as yellow oil (0.29 g, 10.73%).

Step 4: Synthesis of Compound WX012-4

To a solution of compound WX012-3 (290.00 mg, 896.82 mmol), triphenylphosphine (1.18 g, 4.48 mmol) and ziram (891.38 g, 2.91 mmol) in anhydrous THF (10 mL) was added DEAD (780.93 g, 4.48 mmol) dropwise at room temperature under $N_2$ and the mixture was stirred for 12 h at 15° C. After LCMS showed the reaction finished, the mixture was filtered to remove the insoluble and filtrate was concentrated to dry in vacuo. The residue was purified by preparative TLC eluted with Pet. Ether/EtOAc (1/2) to give crude compound WX012-4 (300 mg, containing 30% triphenylphosphine) as yellow solid.

Step 5: Synthesis of Compound WX012

To a solution of compound WX012-4 (300 mg, 0.98 mmol) in EtOH (5 mL) was added aq. LiOH.$H_2$O (412.28 mg, 9.82 mmol) solution (5 mL) at room temperature and the mixture was stirred for 1 h at 15° C. After LCMS showed the reaction finished, pH was adjusted to 5-6 with 1M HCl (aq), and the mixture was extracted with EtOAc (20 mL*3). The organic phase was combined and concentrated to dry in vacuo. The residue was purified by prep HPLC (acidic) to give compound WX012 (10 mg, 3.7%) as white solid.

NMR and MS Data of Embodiments

TABLE 3

| Embodiment | Compound | NMR | MS m/z: |
|---|---|---|---|
| 1 | WX001 | $^1$H NMR (400 MHz, CDCl$_3$) δ: 7.59 (dd, J = 2.6, 9.7 Hz, 1H), 7.54-7.47 (m, 2H), 7.47-7.41 (m, 1H), 7.38 (d, J = 7.3 Hz, 2H), 7.14 (d, J = 2.8 Hz, 1H), 6.74 (d, J = 9.5 Hz, 1H), 4.80 (d, J = 5.8 Hz, 2H), 4.61 (d, J = 5.8 Hz, 2H), 1.67 (s, 3H). | 241.1 242.0 |
| 2 | WX002 | $^1$H NMR (400 MHz, CDCl$_3$) δ: 7.60 (dd, J = 2.5, 9.5 Hz, 1H), 7.46-7.39 (m, 2H), 7.27-7.22 (m, 2H), 6.78 (d, J = 9.5 Hz, 1H), 4.80 (d, J = 6.0 Hz, 2H), 4.63 (d, J = 5.8 Hz, 2H), 1.72-1.65 (m, 1H), 1.69 (s, 2H). | 247.1 247.9 |
| 3 | WX003 | $^1$H NMR (400 MHz, CDCl$_3$) δ = 7.58 (br.d., J = 8.3 Hz, 1H), 7.17 (br.d., J = 19.1 Hz, 3H), 6.74 (br.d., J = 9.5 Hz, 1H), 4.80 (br.d., J = 5.5 Hz, 2H), 4.64 (br.d., J = 5.5 Hz, 2H), 1.69 (s, 3H). | 281.0 281.8 |
| 4 | WX004 | $^1$H NMR (400 MHz, CDCl$_3$) δ = 7.66 (br.dd, J = 2.4, 9.6 Hz, 1H), 7.25 (br.d., J = 2.0 Hz, 1H), 7.15 (s, 1H), 6.88 (br.t., J = 9.6 Hz, 2H), 4.79 (d, J = 6.0 Hz, 2H), 4.63 (d, J = 6.0 Hz, 2H), 2.52 (s, 3H), 1.68 (s, 3H). | 261.1 261.9 |
| 5 | WX005 | $^1$H NMR (400 MHz, CDCl$_3$) δ: 9.18 (d, J = 2.0, 1H), 8.259 (d, J = 2.4, 1H), 8.06 (d, J = 2.4, 1H), 7.64 (dd, J = 2.8, 9.2 Hz, 1H), 6.63 (d, J = 9.6 Hz, 1H), 4.70 (d, J = 6.0 Hz, 2H), 4.50 (d, J = 6.0 Hz, 2H), 1.61 (s, 3H). | 248.3 248.8 |
| 6 | WX006 | $^1$H NMR (400 MHz, MeOD) δ = 8.05-7.92 (m, 1H), 7.88-7.77 (m, 2H), 7.52-7.39 (m, 4H), 6.78 (d, J = 9.5 Hz, 1H), 4.85 (d, J = 5.9 Hz, 2H), 4.59 (d, J = 5.9 Hz, 2H), 1.68 (s, 3H) | 297.4 298.1 |
| 7 | WX007 | $^1$H NMR (400 MHz, MeOD) δ: 7.78 (dd, J = 2.8, 9.2 Hz, 1H), 7.50 (d, J = 2.8, 2H), 7.39 (d, J = 2.4 Hz, 1H), 7.22 (d, J = 2.4 Hz, 1H), 6.71 (d, J = 9.6 Hz, 1H), 4.85 (d, J = 6.0 Hz, 2H), 4.60 (d, J = 6.0 Hz, 2H), 2.05 (s, 3H), 1.69 (s, 3H). | 261.3 262.0 |
| 8 | WX008 | $^1$H NMR (400 MHz, CDCl$_3$) δ: 7.79 (dd, J = 2.5, 9.5 Hz, 1H), 7.55 (d, J = 2.5 Hz, 1H), 7.50-7.39 (m, 3H), 7.33 (d, J = 7.0 Hz, 2H), 6.73 (d, J = 9.5 Hz, 1H), 4.84 (d, J = 7.3 Hz, 2H), 4.74 (d, J = 7.3 Hz, 2H). | 243.1 243.9 |
| 9 | WX009 | $^1$H NMR (400 MHz, CDCl3) δ: 7.78 (dd, J = 2.6, 9.4 Hz, 1H), 7.61 (d, J = 2.3 Hz, 1H), 7.39-7.32 (m, 2H), 7.16 (dd, J = 1.4, 5.1 | 249.1 249.9 |

TABLE 3-continued

| Embodiment | Compound | NMR | MS m/z: |
|---|---|---|---|
| | | Hz, 1H), 6.69 (d, J = 9.3 Hz, 1H), 4.82 (d, J = 7.3 Hz, 2H), 4.67 (d, J = 7.3 Hz, 2H). | |
| 10 | WX010 | $^1$H NMR (400 MHz, CDCl$_3$) δ: 7.50 (dd, J = 2.3, 9.5 Hz, 1H), 7.45-7.32 (m, 4H), 7.29 (d, J = 7.0 Hz, 2H), 6.66 (d, J = 9.5 Hz, 1H), 5.00-4.89 (m, 2H), 4.78-4.67 (m, 2H). | 245.1 246.0 |
| 11 | WX011 | $^1$H NMR (400 MHz, DMSO-d6) δ: 7.52-7.42 (m, 2H), 7.38-7.29 (m, 2H), 7.15 (dd, J = 1.3, 5.0 Hz, 1H), 6.67-6.60 (m, 1H), 4.99-4.89 (m, 2H), 4.77-4.67 (m, 2H). | 251.0 251.9 |
| 12 | WX012 | $^1$H NMR (400 MHz, CDCl$_3$) δ: 7.66 (m, 1H), 7.63(m, 2H), 7.56 (m, 1H), 7.28 (d, J = 4.0 Hz, 1H), 7.16 (m, 2H), 5.16 (d, J = 6.4 Hz, 2H), 4.92 (d, J = 6.4 Hz, 2H). | 277.3 278.1 |

Embodiment 1: Bioactivity Assay
Main task: evaluation on effect of compounds on endotoxin (LPS)-induced TNF-α in rat blood in vitro
Experimental purpose: testing effect of compounds on endotoxin (LPS)-induced TNF-α in rat blood in vitro, and evaluate effect of compounds on endotoxin (LPS)-induced TNF-α in rat blood in vitro
Experimental Materials:
Sprague Dawley rats (male, 210-260 g, Shanghai Slac Laboratory Animal CO. LTD) Rat TNF-alpha Quantikine ELISA Kit (R&D, #SRTA00)
Experimental Process:
A solution of the compound was prepared (5 mM or 1 mM), 40 μL was added into a 48-well cell culture plate, respectively (the final concentration was 0.5 or 0.1 mM). The rats were hocussed with isoflurane and blood was collected from the abdominal aorta (Heparin anticoagulant). The blood was added into a 48-well cell culture plate (320 μL per well) containing the compounds to be tested. And then the 48-well cell culture plate was incubated at 37° C. After 30 min, the plate was added with 40 μL LPS (the final concentration was 100 μg/mL), and then were incubated at 37° C. after mixed. After 5 h, the 48-well plate was taken out and the blood was transferred into 1.5 mL centrifuge tubes and centrifuged in the centrifugal machine (4,500 rpm, 4° C., 5 min). The upper plasma was separated and kept portions (20 μL per well) into 96-well sample plate, and then sharp-frozen and preserved at refrigerator (−80° C.). The second day, the TNF-α level on the blood samples was tested by using R&D ELISA kits according to the kit specification. The data was analyzed by EXCEL and Prism.
Summary of Experimental Results:

TABLE 4

| Embodiment | Inhibition of TNF-α in vitro |
|---|---|
| Pirfenidone* | 51.4% |
| WX001* | 86.3% |
| WX002 | 74.6% |
| WX003 | 84.7% |
| WX004 | 89.5% |
| WX005 | 61.6% |
| WX009* | 51.5% |
| WX011 | 78.8% |

Note:
*means tested concentration of compound was 0.5 Mm, and others was 0.1 mM.

Conclusion: in the experiment of inhibition of TNF-α in vitro, compounds WX001 (0.5 mM), WX002, WX003, WX004, WX011 showed significant inhibition of TNF-α level induced by LPS at 0.1 mM as final concentration which was significantly higher than innovator drug Pirfenidone at the same doge.

Embodiment 2: Efficacy Trial In Vivo
Experimental purpose: test preventive therapeutic effects of compounds on SD rat pulmonary fibrosis induced by Bleomycin
Experimental Materials:
Animal: male SD rat, 35
Model: SD rat pulmonary fibrosis on the left lung; pulmonary fibrosis modelled by injecting Bleomycin into rat trachea
Molding agent: Bleomycin (BLM)
Experimental Process:
1、 experimental grouping: efficacy trial for twice, besides common modeling group and Pirfenidone group as control reference, tested compounds were divided into 3 groups, i.e. model group (Group -1, n=7, Vehicle), control reference drug (group-2, n=7, Pirfenidone); tested compound WX001 group (Group-3, n=7), tested compound WX002 high dosage group (Group-4, n=7), tested compound WX002 low dosage group (Group-5, n=7) (Table 5)

TABLE 5

| group | Animal number | Bleomycin(3.0 mg/kg) | compound | Dosage and frequency |
|---|---|---|---|---|
| Group-1 (trial one) | 7 | Injected | NA | NA |
| Group-2 (trial one) | 7 | Injected | Pirfenidone | 50 mpk, twice a day |
| Group-3 (trial one) | 7 | Injected | WX001 | 30 mpk, twice a day |
| Group-4 (trial two) | 7 | Injected | WX002 | 50 mpk, twice a day |
| Group-5 (trial two) | 7 | Injected | WX002 | 25 mpk, twice a day |

2、 Drug administration: Orally administering on the day the model was established, twice a day and administration for 14 day continuously
3、 Physiological observation of experimental animal: detecting changes in animal weight (test weight before administration every day); detecting animal death rate during test period
4、 euthanasia of animal after 14 days, formalin was injected into left lung to fix, and test volume and weight of left lung after injection and then test Lung Pathology (Table 6)

TABLE 6

| group | Animal number | H&E | Masson Thrichrome dye |
|---|---|---|---|
| Group-1 (trial one) | 7 | Needed | Needed |
| Group-2 (trial one) | 7 | Needed | Needed |
| Group-3 (trial one) | 7 | Needed | Needed |
| Group-4 (trial two) | 7 | Needed | Needed |
| Group-5 (trial two) | 7 | Needed | Needed |

Test Results of Experiment:
Test of tissue pathology of left lung: pathological evaluation of H&E dye: 1) pathological changes of left lung terminal bronchiole, 2) pathological changes of left lung pulmonary arteriole; pathological evaluation of Masson Thrichrome dye: 3) area of left lung pulmonary fibrosis, 4) score of left lung pulmonary fibrosis.

Figure 2:
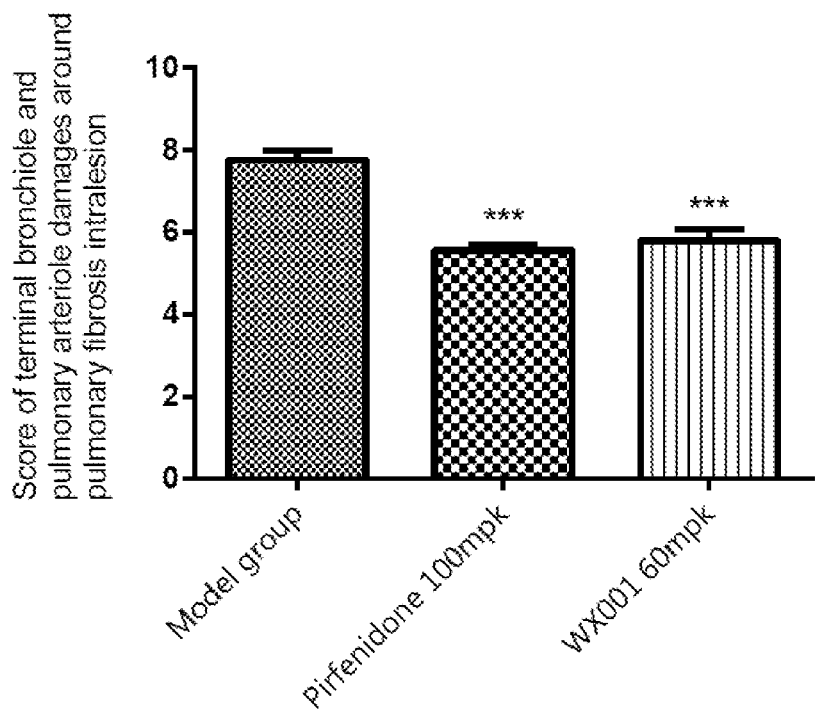
FIG. 2 is grade of WX001 improving tissue damage around the border of pulmonary fibrosis area
Figure 3:
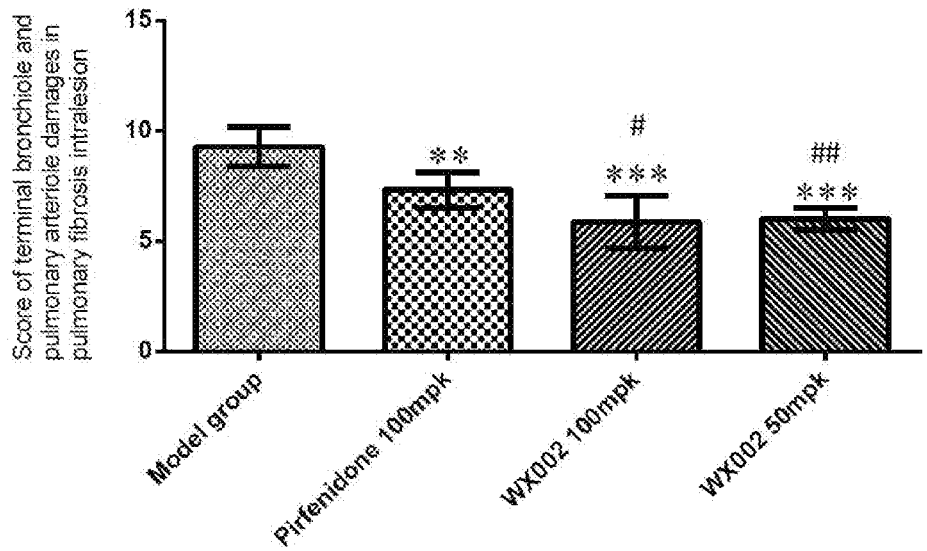
FIG. 3 is grade of WX002 improving tissue damage in the area of pulmonary fibrosis
Figure 4:
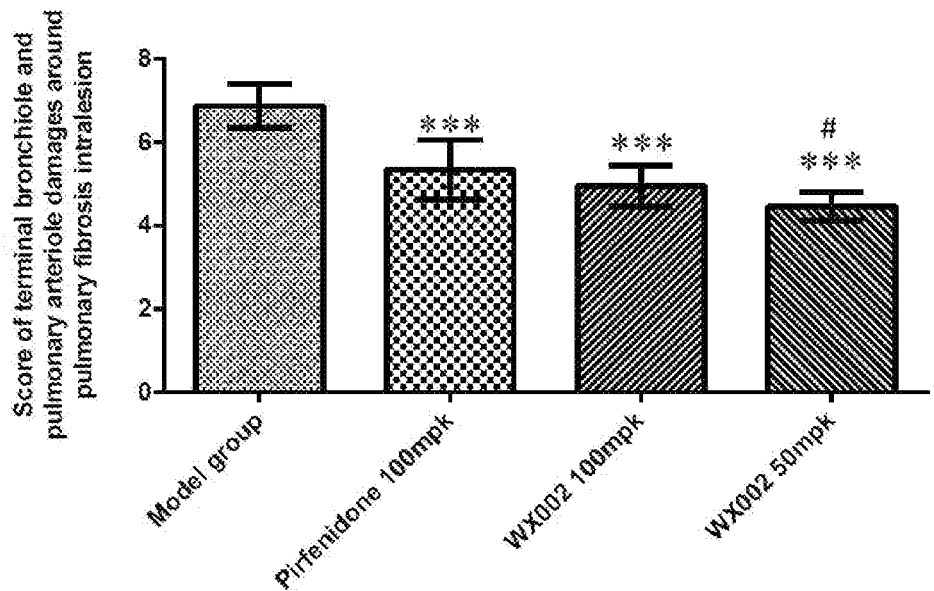
FIG. 4 is grade of WX002 improving tissue damage around the border of pulmonary fibrosis area
Figure 5:
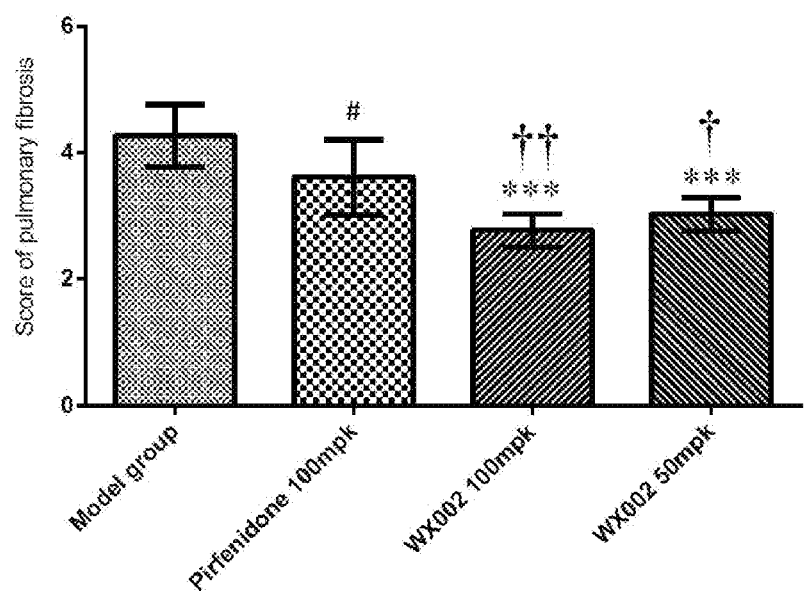
FIG. 5 is effective grade of WX002 preventing the area of pulmonary fibrosis

Conclusion of Experimental Results:
The results of the second pharmacodynamic test showed that WX001 had a good effect on improving tissue damage in the area and margin of pulmonary fibrosis lesions (FIGS. 1&2). WX002 also had a good effect on improving tissue damage in the area and margin of pulmonary fibrosis lesions (FIGS. 3&4) which had a good effect in preventing the formation of pulmonary fibrosis (FIG. 5). Compared with the reference compound Pirfenidone, both the same dose of 100 mpk group and the low dose of 50 mpk group achieved better efficacy than Pirfenidone.

What is claimed is:

1. A compound shown in formula (I), a pharmaceutically acceptable salt and a tautomer thereof,

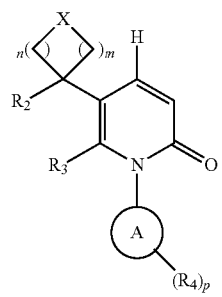
(I)

wherein:
X is selected from O, S, and N(R);
R$_2$ is selected from F, Cl, Br, I, OH, NH$_2$, CN, NO$_2$, and COOH, or is selected from the group consisting of C$_{1-6}$ alkyl and C$_{1-6}$ heteroalkyl, the C$_{1-6}$ alkyl and C$_{1-6}$ heteroalkyl being optionally substituted with 1, 2 or 3 of R;
R$_3$ is H, or is selected from the group consisting of C$_{1-6}$ alkyl and C$_{1-6}$ heteroalkyl, the C$_{1-6}$ alkyl and C$_{1-6}$ heteroalkyl being optionally substituted with 1, 2 or 3 of R;
R$_4$ is selected from F, Cl, Br, I, OH, NH$_2$, NO$_2$, CN, and COOH, or is selected from the group consisting of C$_{1-6}$ alkyl and C$_{1-6}$ heteroalkyl, the C$_{1-6}$ alkyl and C$_{1-6}$ heteroalkyl being optionally substituted with 1, 2 or 3 of R;
Ring A is selected from 5-10-membered aryl and 5-10-membered heteroaryl;
m is selected from 0, 1 or 2;
n is selected from 0, 1 or 2;
m and n are not 0 at the same time;
p is selected from 0, 1, 2 or 3;
R is selected from H, F, Cl, Br, I, OH, CN, NH$_2$, COOH, and C(=O)NH$_2$, or is selected from the group consisting of C$_{1-8}$ alkyl, C$_{1-8}$ heteroalkyl, C$_{3-6}$ cycloalkyl, 3 to 6-membered heterocycloalkyl and C$_{3-6}$ cycloalkyl-C$_{1-3}$ alkyl-, the C$_{1-8}$ alkyl, C$_{1-8}$ heteroalkyl, C$_{3-6}$ cycloalkyl, 3 to 6-membered heterocycloalkyl and C$_{3-6}$ cycloalkyl-C$_{1-3}$ alkyl being optionally substituted with 1, 2 or 3 of R'; and
R' is selected from F, Cl, Br, I, OH, CN, NH$_2$, COOH, Me, Et, CF$_3$, CHF$_2$, CH$_2$F, NHCH$_3$, and N(CH$_3$)$_2$,
wherein "hetero" means hetero atom or hetero atom group, which is selected from the group consisting of —C(=O)N(R)—, —N(R)—, —C(=NR)—, —S(=O)$_2$N(R)—, —S(=O)N(R), —O—, —S—, =O, =S, —O—N=, —C(=O)O—, —C(=O)—, —C(=S)—, —S(=O)—, —S(=O)$_2$— and —N(R)C(=O)N(R)—, and
wherein in any case above, the number of hetero atom or hetero group is independently selected from 1, 2 or 3, respectively.

2. The compound, pharmaceutically acceptable salt and tautomer thereof of claim 1, wherein R is selected from H, F, Cl, Br, I, OH, CN, NH$_2$, COOH, and C(=O)NH$_2$, or is selected from the group consisting of C$_{1-3}$ alkyl, C$_{1-3}$ alkyl-O—, C$_{1-3}$ alkyl-S—, C$_{1-3}$ alkyl-NH—, N,N'-di(C$_{1-3}$ alkyl)amino, C$_{3-6}$ cycloalkyl and 3-6-membered heterocycloalkyl, the C$_{1-3}$ alkyl, C$_{1-3}$ alkyl-O—, C$_{1-3}$ alkyl-S—, C$_{1-3}$ alkyl-NH—, N,N'-di(C$_{1-3}$ alkyl)amino, C$_{3-6}$ cycloalkyl and 3-6-membered heterocycloalkyl being optionally substituted with 1, 2 or 3 of R'.

3. The compound, pharmaceutically acceptable salt and tautomer thereof of claim 2, wherein R is selected from H, F, Cl, Br, I, OH, CN, NH$_2$, COOH, C(=O)NH$_2$, Me, Et, CF$_3$, CHF$_2$, CH$_2$F, NH(CH$_3$), and N(CH$_3$)$_2$.

4. The compound, pharmaceutically acceptable salt and tautomer thereof of claim 1, wherein structural unit

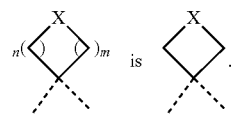

5. The compound, pharmaceutically acceptable salt and tautomer thereof of claim 4, wherein the structural unit

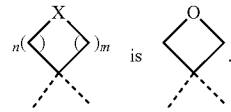

6. The compound, pharmaceutically acceptable salt and tautomer thereof of claim 1, wherein R$_2$ is selected from F, Cl, Br, I, OH, NH$_2$, CN, NO$_2$, and COOH, or is C$_{1-3}$ alkyl which is optionally substituted with 1, 2 or 3 of R.

7. The compound, pharmaceutically acceptable salt and tautomer thereof of claim 6, wherein R$_2$ is selected from F, Cl, Br, I, OH, NH$_2$, CN, NO$_2$, and COOH, or is Me which is optionally substituted with 1, 2 or 3 of R.

8. The compound, pharmaceutically acceptable salt and tautomer thereof of claim 7, wherein R$_2$ is selected from F, Cl, Br, I, OH, NH$_2$, CN, NO$_2$, COOH, and Me.

9. The compound, pharmaceutically acceptable salt and tautomer thereof of claim 1, wherein R$_4$ is selected from F, Cl, Br, I, OH, NH$_2$, NO$_2$, CN, and COOH, or is selected from the group consisting of C$_{1-3}$ alkyl, C$_{1-3}$ alkoxy, C$_{1-3}$ alkylthio, NH(C$_{1-3}$ alkyl) and N,N'-di(C$_{1-2}$ alkyl)amino, the C$_{1-3}$ alkyl, C$_{1-3}$ alkoxy, C$_{1-3}$ alkylthio, NH(C$_{1-3}$ alkyl) and N,N'-di(C$_{1-2}$ alkyl)amino being optionally substituted with 1, 2 or 3 of R.

10. The compound, pharmaceutically acceptable salt and tautomer thereof of claim 9, wherein R$_4$ is selected from F, Cl, Br, I, OH, NH$_2$, NO$_2$, CN, and COOH, or is selected from the group consisting of Me and

the Me and

being optionally substituted with 1, 2 or 3 of R.

11. The compound, pharmaceutically acceptable salt and tautomer thereof of claim 10, wherein $R_4$ is selected from F, Cl, Br, I, OH, $NH_2$, $NO_2$, CN, COOH, Me,

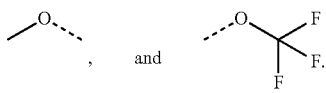

12. The compound, pharmaceutically acceptable salt and tautomer thereof of claim 1, wherein ring A is selected from 5-6-membered aryl and 5-9-membered heteroaryl.

13. The compound, pharmaceutically acceptable salt and tautomer thereof of claim 12, wherein ring A is selected from pheny I, pyridinyl, pyrazinyl, pyrimidyl, pyridaziny, pyrryl, imidazolyl, pyrazolyl, furyl, thienyl, oxazolyl, thiazolyl, isoxazolyl, isothiazolyl, truazolyl, and benzothienyl.

14. The compound, pharmaceutically acceptable salt and tautomer thereof of claim 13, wherein structural unit

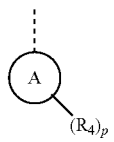

is selected from

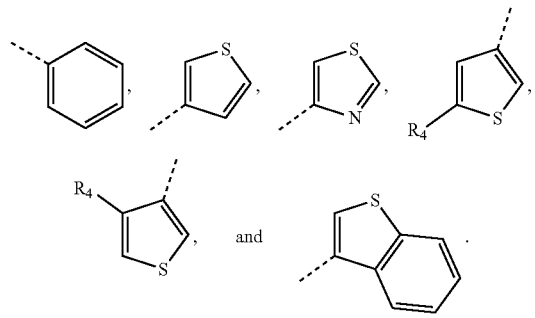

15. The compound, pharmaceutically acceptable salt and tautomer thereof of claim 11, wherein structural unit

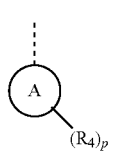

is selected from

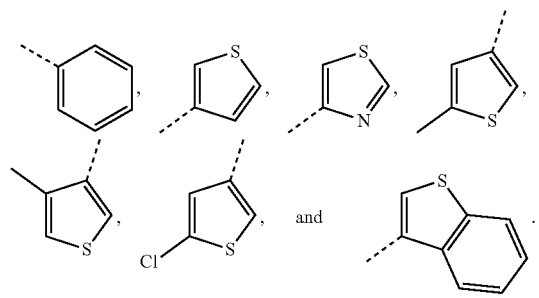

16. The compound, pharmaceutically acceptable salt and tautomer thereof of claim 1, which is selected from (I-1)

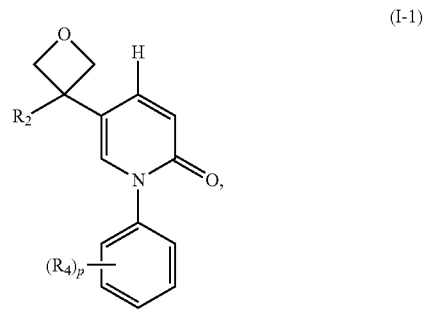

(I-2)

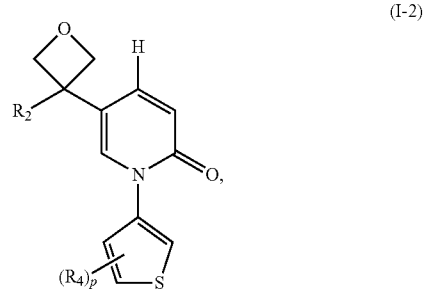

(I-3)

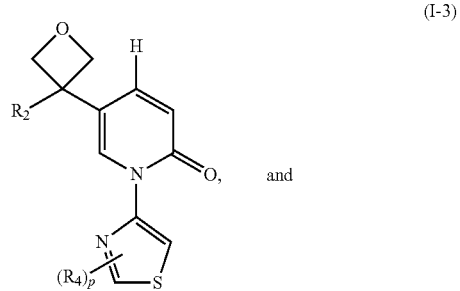

and (I-4)

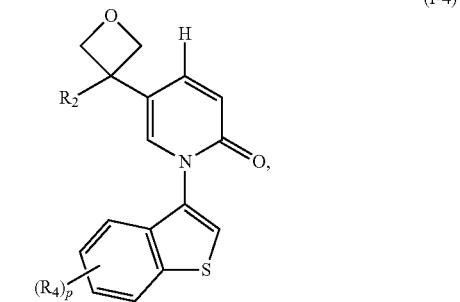

wherein $R_2$, $R_4$ and p are as defined as claim 1.

17. A compound selected from:

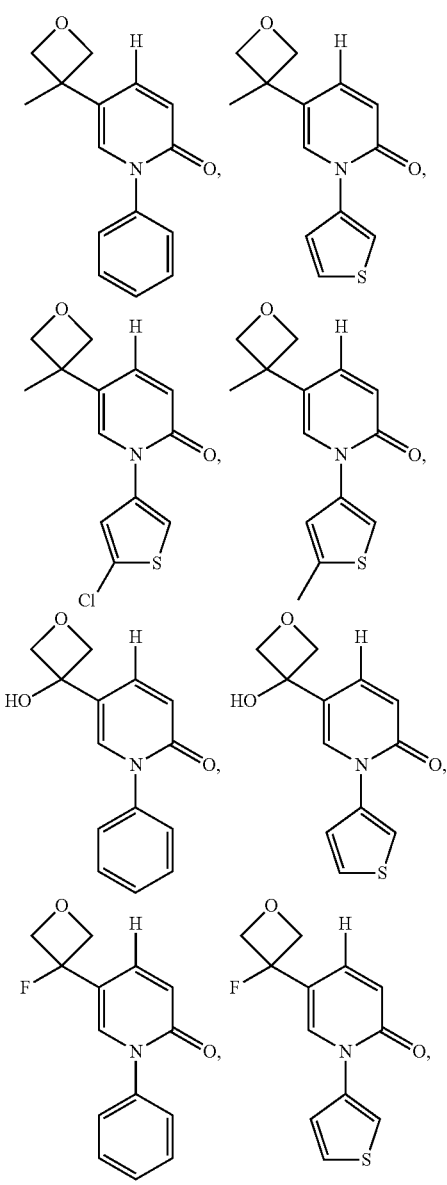

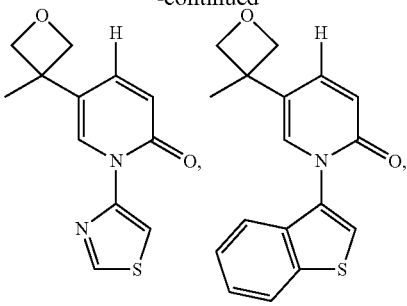

18. A pharmaceutical composition, comprising an effective amount of the compound or pharmaceutically acceptable salt thereof of claim 1 and a pharmaceutically acceptable carrier.

19. A method for treating fibrosis-related diseases in a subject in need thereof, the method comprising administering a pharmaceutically effective amount of the compound or pharmaceutically acceptable salt thereof of claim 1 to the subject.

20. The method of claim 19, wherein the fibrosis-related diseases is idiopathic pulmonary fibrosis.

21. The method of claim 19, wherein the fibrosis-related diseases is liver fibrosis.

\* \* \* \* \*